United States Patent
Wondka et al.

(10) Patent No.: US 10,499,819 B2
(45) Date of Patent: Dec. 10, 2019

(54) BREATH SELECTION FOR ANALYSIS

(71) Applicant: Capnia, Inc., Palo Alto, CA (US)

(72) Inventors: Anthony D. Wondka, San Ramon, CA (US); Anish Bhatnagar, Redwood City, CA (US); Scott J. Gilbert, Menlo Park, CA (US)

(73) Assignee: CAPNIA, INC., Foster City, CA (US)

( * ) Notice: Subject to any disclaimer, the term of this patent is extended or adjusted under 35 U.S.C. 154(b) by 201 days.

(21) Appl. No.: 14/150,625

(22) Filed: Jan. 8, 2014

(65) Prior Publication Data

US 2014/0194703 A1 Jul. 10, 2014

Related U.S. Application Data

(60) Provisional application No. 61/750,305, filed on Jan. 8, 2013.

(51) Int. Cl.
| | |
|---|---|
| A61B 5/0205 | (2006.01) |
| A61B 5/00 | (2006.01) |
| A61B 5/08 | (2006.01) |
| G16H 50/20 | (2018.01) |
| G16H 10/40 | (2018.01) |

(Continued)

(52) U.S. Cl.
CPC .......... *A61B 5/02055* (2013.01); *A61B 5/082* (2013.01); *A61B 5/7221* (2013.01); *A61B 5/7275* (2013.01); *G16H 10/40* (2018.01); *G16H 40/63* (2018.01); *G16H 50/20* (2018.01); *A61B 5/01* (2013.01); *A61B 5/087* (2013.01); *A61B 5/0816* (2013.01); *A61B 5/091* (2013.01); *A61B 5/7203* (2013.01); *A61B 5/7285* (2013.01); *A61B 2560/0223* (2013.01)

(58) Field of Classification Search
CPC ......... A61B 5/082; A61B 5/087; A61B 5/091; A61B 5/00; G06F 19/30
See application file for complete search history.

(56) References Cited

U.S. PATENT DOCUMENTS

| | | | |
|---|---|---|---|
| 2,073,192 A | 3/1937 | Connell | |
| 3,306,283 A | 2/1967 | Arp | |

(Continued)

FOREIGN PATENT DOCUMENTS

| | | |
|---|---|---|
| CN | 1097120 A | 1/1995 |
| CN | 101098726 A | 1/2008 |

(Continued)

OTHER PUBLICATIONS

International Search Report and Written Opinion for PCT/US14/53569, dated Feb. 17, 2015, 18 pages.

(Continued)

*Primary Examiner* — Carl H Layno
*Assistant Examiner* — Dacheng Xie
(74) *Attorney, Agent, or Firm* — Cooley LLP

(57) ABSTRACT

Methods and systems are described to obtain and analyze a gas sample from a desired section of the breath of a person, while accounting for erratic, episodic or otherwise challenging breathing patterns that may otherwise make the capturing of a gas sample from the desired section of breath difficult. These techniques may provide more reliable, accurate and adequate samples of gas such as end-tidal gas, and ultimately an accurate analysis of the sample captured.

12 Claims, 12 Drawing Sheets

(51) Int. Cl.
  *G16H 40/63* (2018.01)
  *A61B 5/01* (2006.01)
  *A61B 5/087* (2006.01)
  *A61B 5/091* (2006.01)

(56) References Cited

U.S. PATENT DOCUMENTS

| | | | |
|---|---|---|---|
| 3,343,529 | A | 9/1967 | Miller et al. |
| 3,858,573 | A | 1/1975 | Ryan et al. |
| 3,910,261 | A | 10/1975 | Ragsdale et al. |
| 4,440,177 | A | 4/1984 | Anderson et al. |
| 4,619,269 | A | 10/1986 | Cutlet et al. |
| 4,671,298 | A | 6/1987 | Babb et al. |
| 5,003,985 | A | 4/1991 | White et al. |
| 5,069,220 | A | 12/1991 | Casparie et al. |
| 5,072,737 | A | 12/1991 | Goulding |
| 5,129,401 | A | 7/1992 | Corenman et al. |
| 5,285,794 | A | 2/1994 | Lynch |
| 5,357,971 | A | 10/1994 | Sheehan et al. |
| 5,361,771 | A | 11/1994 | Craine et al. |
| 5,361,772 | A | 11/1994 | Murnick et al. |
| 5,363,857 | A | 11/1994 | Howard |
| 5,383,469 | A | 1/1995 | Vreman et al. |
| 5,533,512 | A | 7/1996 | Novotny et al. |
| 5,533,513 | A | 7/1996 | Ueda et al. |
| 5,573,005 | A | 11/1996 | Ueda et al. |
| 5,924,995 | A | 7/1999 | Klein et al. |
| 5,971,934 | A | 10/1999 | Scherer et al. |
| 6,010,459 | A | 1/2000 | Silkoff et al. |
| 6,251,082 | B1 | 6/2001 | Rayburn |
| 6,278,975 | B1 | 8/2001 | Brant et al. |
| 6,428,483 | B1 | 8/2002 | Carlebach |
| 6,544,190 | B1 | 4/2003 | Smits et al. |
| 6,582,376 | B2 | 6/2003 | Pranalytica |
| 6,620,107 | B2 | 9/2003 | Payne et al. |
| 6,733,463 | B2 | 5/2004 | Moilanen et al. |
| 6,739,335 | B1 | 5/2004 | Rapport et al. |
| 6,799,575 | B1 | 10/2004 | Carter |
| 7,063,667 | B1 | 6/2006 | Ben-Oren et al. |
| 7,191,000 | B2 | 3/2007 | Zhu et al. |
| 7,223,244 | B1 | 5/2007 | Koh |
| 7,600,439 | B1 | 10/2009 | Patterson et al. |
| 7,775,210 | B2 | 8/2010 | Schobel (nee Bauer) et al. |
| 8,021,308 | B2 | 9/2011 | Capnia |
| 8,251,914 | B2 | 8/2012 | Daniels et al. |
| 8,485,984 | B2 | 7/2013 | Giron et al. |
| 8,679,029 | B2 | 3/2014 | Krauss et al. |
| 9,655,543 | B2 | 5/2017 | Aoki et al. |
| 10,034,621 | B2 | 7/2018 | Wondka et al. |
| 2001/0037070 | A1 | 11/2001 | Cranley et al. |
| 2002/0138213 | A1 | 9/2002 | Mault |
| 2002/0151814 | A1 | 10/2002 | Payne et al. |
| 2003/0008407 | A1 | 1/2003 | Fu |
| 2003/0191405 | A1 | 10/2003 | Rich et al. |
| 2003/0208133 | A1 | 11/2003 | Mault |
| 2004/0077995 | A1 | 4/2004 | Ferek-Petric et al. |
| 2004/0210154 | A1 | 10/2004 | Kline |
| 2005/0137491 | A1 | 6/2005 | Paz et al. |
| 2005/0177056 | A1* | 8/2005 | Giron ............... A61M 16/0666 600/543 |
| 2006/0094964 | A1 | 5/2006 | Ragauskas et al. |
| 2006/0133960 | A1 | 6/2006 | Ahmad |
| 2006/0178592 | A1 | 8/2006 | Nason et al. |
| 2006/0195040 | A1 | 8/2006 | Nason et al. |
| 2006/0200037 | A1 | 9/2006 | Falasco |
| 2006/0241507 | A1* | 10/2006 | Carlson ............... A61B 5/083 600/532 |
| 2006/0253045 | A1* | 11/2006 | Coifman ............ A61B 5/0871 600/538 |
| 2007/0073182 | A1 | 3/2007 | Wilson |
| 2007/0129647 | A1 | 6/2007 | Lynn |
| 2007/0167853 | A1 | 7/2007 | Melker et al. |
| 2007/0173731 | A1 | 7/2007 | Meka et al. |
| 2007/0261472 | A1 | 11/2007 | Flaherty et al. |
| 2008/0009762 | A1 | 1/2008 | Hampton et al. |
| 2008/0038154 | A1 | 2/2008 | Longbottom et al. |
| 2008/0119753 | A1 | 5/2008 | Ricciardelli et al. |
| 2008/0121230 | A1 | 5/2008 | Cortez et al. |
| 2009/0044805 | A1 | 2/2009 | Somaiya et al. |
| 2009/0187113 | A1 | 7/2009 | Friedman et al. |
| 2009/0246891 | A1 | 10/2009 | Sato et al. |
| 2009/0247891 | A1 | 10/2009 | Wood |
| 2010/0317986 | A1 | 12/2010 | Colman et al. |
| 2011/0004108 | A1* | 1/2011 | Peyton ............... A61B 5/029 600/484 |
| 2011/0021942 | A1 | 1/2011 | Choe et al. |
| 2011/0066060 | A1 | 3/2011 | Von Bahr et al. |
| 2011/0196295 | A1 | 8/2011 | Gonzalez et al. |
| 2011/0257550 | A1 | 10/2011 | Choi |
| 2011/0263947 | A1 | 10/2011 | Utley et al. |
| 2012/0055481 | A1 | 3/2012 | Orr et al. |
| 2012/0090378 | A1 | 4/2012 | Wang et al. |
| 2012/0215125 | A1* | 8/2012 | Orr ............... A61B 5/0816 600/532 |
| 2012/0247471 | A1* | 10/2012 | Masic ............ A61M 16/0051 128/204.23 |
| 2012/0302908 | A1 | 11/2012 | Hemnes et al. |
| 2012/0310104 | A1 | 12/2012 | Van Kesteren et al. |
| 2013/0165806 | A1 | 6/2013 | Wondka et al. |
| 2013/0217029 | A1 | 8/2013 | Sislian et al. |
| 2013/0267862 | A1 | 10/2013 | Jaffe et al. |
| 2014/0228699 | A1 | 8/2014 | Causevic |
| 2015/0065900 | A1 | 3/2015 | Wondka et al. |
| 2015/0065901 | A1 | 3/2015 | Bhatnagar et al. |
| 2015/0265184 | A1 | 9/2015 | Wondka et al. |
| 2016/0106343 | A1 | 4/2016 | Wondka et al. |
| 2019/0024632 | A1 | 1/2019 | Causevic et al. |

FOREIGN PATENT DOCUMENTS

| | | |
|---|---|---|
| CN | 101214151 A | 7/2008 |
| CN | 101366672 A | 2/2009 |
| CN | 101547716 A | 9/2009 |
| CN | 101636109 A | 1/2010 |
| CN | 201692453 U | 1/2011 |
| CN | 102188241 A | 9/2011 |
| CN | 102770069 A | 11/2012 |
| EP | 0 574 027 A2 | 12/1993 |
| EP | 0 648 088 A1 | 4/1995 |
| EP | 1 480 557 | 12/2004 |
| EP | 0892926 | 12/2006 |
| EP | 2 066 236 A2 | 6/2009 |
| EP | 2293056 | 3/2011 |
| EP | 1850748 | 8/2011 |
| GB | 2 472 116 A | 1/2011 |
| JP | S-49-009085 A | 1/1974 |
| JP | S-61-100231 A | 5/1986 |
| JP | 6-58919 A | 3/1994 |
| JP | H-7-116145 A | 5/1995 |
| JP | A-11-160311 A | 6/1999 |
| JP | 2003-529044 A | 9/2003 |
| JP | 2005-519272 A | 6/2005 |
| JP | A-2008-530532 A | 8/2008 |
| JP | 2009-058398 A | 3/2009 |
| JP | 2009-545408 A | 12/2009 |
| JP | 2010-233611 A | 10/2010 |
| WO | WO-97/43952 A1 | 11/1997 |
| WO | WO-00/063683 A1 | 10/2000 |
| WO | WO-03/073935 A2 | 9/2003 |
| WO | WO-03/073935 A3 | 9/2003 |
| WO | WO-2004/032719 A2 | 4/2004 |
| WO | WO-2004/032719 A3 | 4/2004 |
| WO | WO-2006/086323 A1 | 8/2006 |
| WO | WO-2007/059263 A2 | 5/2007 |
| WO | WO-2007/059263 A3 | 5/2007 |
| WO | WO-2008/019294 A2 | 2/2008 |
| WO | WO-2008/019294 A3 | 2/2008 |
| WO | WO-2008/019680 A2 | 2/2008 |
| WO | WO-2008/019680 A3 | 2/2008 |
| WO | WO-2008/060165 A1 | 5/2008 |
| WO | WO-2008/081449 A2 | 7/2008 |
| WO | WO-2008/081449 A3 | 7/2008 |
| WO | WO-2008/112927 A2 | 9/2008 |
| WO | WO-2008/112927 A3 | 9/2008 |

(56) References Cited

FOREIGN PATENT DOCUMENTS

| WO | WO-2010/097716 A1 | 9/2010 |
|---|---|---|
| WO | WO-2011/055250 A2 | 5/2011 |
| WO | WO-2011/055250 A3 | 5/2011 |
| WO | WO-2011/070472 A1 | 6/2011 |
| WO | WO-2011/101776 A1 | 8/2011 |
| WO | WO-2012/053910 | 4/2012 |
| WO | WO-2012/059768 | 5/2012 |
| WO | WO-2012/076614 | 6/2012 |
| WO | WO-2012/146991 A1 | 11/2012 |
| WO | WO-2013/003429 A1 | 1/2013 |
| WO | WO-2013/096695 A2 | 6/2013 |
| WO | WO-2013/096695 A3 | 6/2013 |
| WO | WO-2014/110181 A1 | 7/2014 |
| WO | WO-2014/127044 A1 | 8/2014 |
| WO | WO-2015/031848 A2 | 3/2015 |
| WO | WO-2015/031848 A3 | 3/2015 |
| WO | WO-2015/031850 A1 | 3/2015 |
| WO | WO-2015/143384 A1 | 9/2015 |
| WO | WO-2016/064925 A1 | 4/2016 |

OTHER PUBLICATIONS

International Search Report and Written Opinion for PCT/US12/71085, dated May 13, 2013, 10 pages.
International Search Report and Written Opinion for PCT/US2014/016105, dated Apr. 30, 2014, 7 pages.
International Search Report and Written Opinion for PCT/US2014/053567 dated Dec. 18, 2014, 15 pages.
International Search Report and Written Opinion for PCT/US14/53572, dated Dec. 24, 2014, 8 pages.
Medtronic Capnography brochure MIN 3012492-001/CAT 21300-001569.
Molloy et al., "Are carbon dioxide detectors useful in neonates?" Arch Dis Child Fetal Neonatal Ed (2006) 91:F295-F298.
International Search Report and Written Opinion for PCT/US14/10746, dated Apr. 15, 2014, 8 pages.
Bartlett, R.G. et al. (1957). "Maximum breathing capacity with various expiratory and inspiratory resistances (single and combined) at various breathing rates," J. Appl. Physiol. 11(1):79-83.
Extended European Search Report dated Feb. 26, 2016, for European Patent Application No. 12 860 711.6, filed on Dec. 20, 2012, 6 pages.
Extended European Search Report dated Sep. 30, 2016, for European Patent Application No. 14 751 436.8, filed on Feb. 12, 2014, 8 pages.
Final Office Action dated Aug. 24, 2016, for U.S. Appl. No. 13/722,950, filed Dec. 20, 2012, 11 pages.
International Search Report dated Jul. 2, 2015, for PCT Application No. PCT/US2015/021852, filed on Mar. 20, 2015, 2 pages.
International Search Report dated Feb. 9, 2016, for PCT Application No. PCT/US2015/056527, filed on Oct. 20, 2015, 4 pages.
Jaffe, M.B. (2002). "Mainstream of sidestream capnography?" Medical device depot Inc., White paper, 14 total pages.
Non-Final Office Action dated Dec. 1, 2015, for U.S. Appl. No. 13/722,950, filed Dec. 20, 2012, 7 pages.
Non-Final Office Action dated Oct. 21, 2016, for U.S. Appl. No. 14/473,888, filed Aug. 29, 2014, 22 pages.
Non-Final Office Action dated Nov. 10, 2016, for U.S. Appl. No. 14/179,381, filed Feb. 12, 2014, 12 pages.
Written Opinion of the International Searching Authority dated May 13, 2013, for PCT Application No. PCT/US2012/071085, filed on Dec. 20, 2012, 6 pages.
Written Opinion of the International Searching Authority dated Apr. 15, 2014, for PCT Application No. PCT/US2014/010746, filed on Jan. 8, 2014, 6 pages.
Written Opinion of the International Searching Authority dated Apr. 30, 2014, for PCT Application No. PCT/US2014/016105, filed on Feb. 12, 2014, 5 pages.
Written Opinion of the International Searching Authority dated Feb. 17, 2015, for PCT Application No. PCT/US2014/053569, filed on Aug. 29, 2014, 6 pages.
Written Opinion of the International Searching Authority dated Dec. 18, 2014, for PCT Application No. PCT/US2014/053567, filed on Aug. 29, 2014, 5 pages.
Written Opinion of the International Searching Authority dated Dec. 24, 2014, for PCT Application No. PCT/US2014/053572, filed on Aug. 29, 2014, 5 pages.
Written Opinion of the International Searching Authority dated Jul. 2, 2015, for PCT Application No. PCT/US2015/021852, filed on Mar. 20, 2015, 8 pages.
Written Opinion of the International Searching Authority dated Feb. 9, 2016, for PCT Application No. PCT/US2015/056527, filed on Oct. 20, 2015, 6 pages.
Extended European Search Report dated Jun. 8, 2016, for European Patent Application No. 14 737 690.9, filed on Jan. 8, 2014, 9 pages.
Extended European Search Report dated Mar. 16, 2017, for European Patent Application No. 14 839 697.1, filed on Aug. 29, 2014, 9 pages.
Extended European Search Report dated Jul. 12, 2017, for European Patent Application No. 14 838 958.8, filed on Aug. 29, 2014, 11 pages.
Final Office Action dated Jun. 7, 2017, for U.S. Appl. No. 14/473,888, filed Aug. 29, 2014, 16 pages.
Final Office Action dated Aug. 16, 2017, for U.S. Appl. No. 14/179,381, filed Feb. 12, 2014, 11 pages.
Non-Final Office Action dated Mar. 13, 2017, for U.S. Appl. No. 13/722,950, filed Dec. 20, 2012, 7 pages.
Non-Final Office Action dated Mar. 23, 2017, for U.S. Appl. No. 14/664,728, filed Mar. 20, 2015, 18 pages.
Non-Final Office Action dated Apr. 20, 2017, for U.S. Appl. No. 14/473,878, filed Aug. 29, 2014, 10 pages.
Partial Supplementary European Search Report dated Apr. 7, 2017, for European Patent Application No. 14 838 958.8, filed on Aug. 29, 2014, 7 pages.
Coburn, R.F. et al. (1966). "Endogenous Carbon Monoxide Production in Patients with Hemolytic Anemia," Journal of Clinical Investigation 45:460-468.
Ebola Virus Infection (2017). Doctor-clinic.org, 2 total pages.
Extended European Search Report dated Oct. 16, 2017, for European Patent Application No. 15 764 503.7, filed on Mar. 20, 2015, 8 pages.
Final Office Action dated Oct. 19, 2017, for U.S. Appl. No. 14/664,728, filed Mar. 20, 2015, 18 pages.
Final Office Action dated Nov. 20, 2017, for U.S. Appl. No. 14/473,878, filed Aug. 29, 2014, 11 pages.
Final Office Action dated Dec. 29, 2017, for U.S. Appl. No. 13/722,950, filed Dec. 20, 2012, 5 pages.
Final Office Action dated Jun. 5, 2018, for U.S. Appl. No. 14/473,878, filed Aug. 29, 2014, 10 pages.
Non-Final Office Action dated Dec. 15, 2017, for U.S. Appl. No. 14/918,484, filed Oct. 20, 2015, 15 pages.
Non-Final Office Action dated Jan. 8, 2018, for U.S. Appl. No. 14/473,888, filed Aug. 29, 2014, 16 pages.
Notice of Allowance dated Mar. 30, 2018, for U.S. Appl. No. 13/722,950, filed Dec. 20, 2012, 7 pages.
Final Office Action dated Aug. 24, 2018, for U.S. Appl. No. 14/473,888, filed Aug. 29, 2014, 11 pages.
Non-Final Office Action dated Oct. 18, 2018, for U.S. Appl. No. 14/664,728, filed Mar. 20, 2015, 23 pages.
Non-Final Office Action dated Jan. 10, 2019, for U.S. Appl. No. 14/473,878, filed Aug. 29, 2014, 9 pages.
Restek Product catalog 2011/2012 https://www.calameo.com/books/00004252746f79e5d8c85 (Year: 2012), 1 total page.

* cited by examiner

BREATH SELECTION FOR ANALYSIS

CROSS-REFERENCE TO RELATED APPLICATIONS

This application claims the benefit of U.S. Provisional Application No. 61/750,305 filed on, Jan. 8, 2013, the disclosure of which is hereby incorporated by reference in its entirety.

FIELD

Described herein are devices and methods for the analysis of breath exhalant for diagnostic purposes. More specifically, devices and methods are described for identifying a physiologically relevant portion of a breathing cycle, which may be used to correlate the analysis of the exhalant to an underlying physiologic condition.

BACKGROUND

Certain metabolites and chemicals produced in or entering the body and bloodstream are excreted in the breath. The level in the body or blood stream may be determined by measuring it in the breath. For example, breath CO levels may be measured to detect and monitor underlying disorders such as hematological disorders and conditions, metabolic disorders, and environmental and behavioral problems. For example, end-tidal CO can be correlated to blood CO, which can be indicative of hemolysis, smoking or inhalation poisoning. In order to measure end-tidal CO, alveolar gas may be collected non-invasively from the exhaled breath of a patient by capturing the portion of the breath at the end of exhalation. The captured end-tidal gas can then be analyzed for its CO concentration thus completing the non-invasive diagnostic measurement. Typically, a correlation exists between the level of an analyte in the exhaled gas and the level of a metabolite or chemical or other substance in the body or blood, for example a 1:1 ratio or some other ratio.

It has been discovered that proper and accurate correlation of blood-to-breath analyte levels, such as CO gas, may be dependent on the breathing pattern. Typically, breath samples are taken without contemplating whether or not the patient's breathing pattern is appropriate for the diagnostic analysis being taken. When the level of a certain gas in the blood is being analyzed by measuring it in the breath, in some situations, in order for the correlation of blood-to-breath level to be accurate, the patient may need to be breathing at their normal resting tidal volume or minute volume breathing pattern in terms of frequency and depth of breathing. In other situations, the blood-to-breath correlation may be more accurate if the person performs a non-resting tidal volume breath, such as a sigh breath or breath hold (for example when attempting to diagnose a metabolic disorder), or deep breath (for example when attempting to diagnose an infection).

In addition, it may be beneficial during a breath test, that the end-tidal gas be collected automatically or semi-automatically from a non-cooperative patient or a patient incapable of following instructions. Or in some cases a patient that may be capable of cooperating, but is influenced by the test, and inadvertently may submit a sample when breathing abnormally. In these situations, obtaining a pure and adequate sample of gas from the breath can be challenging.

SUMMARY

To address the above deficiencies, the present disclosure provides systems and methods that define, target, capture, and analyze a physiologically appropriate breath or breaths for the diagnostic test being undertaken, and may avoid the analysis of physiologically inappropriate breaths that could lead to a false diagnostic result.

Described herein are breath analyte analyzers and methods that may reliably collect an accurate sample of exhalant analyte such as end-tidal gas from a wide-range of breathing patterns and may encompass a wide-range of patient types, environmental conditions, and clinical circumstances. In a first variation, a breathing pattern is measured for a period of time until a certain type of breath occurs. The type of breath desired may be predefined by establishing breath threshold criteria for which an accurate sample may be obtained. The threshold criteria may be, for example, detection of a complete and normal tidal volume breath of the patient. Once a threshold criteria is met, a sample may be taken from the appropriate portion of that corresponding breath. In a second variation, a sample is collected from a breath that meets one of two or more predefined types of breaths. For example a breath with an expiratory period of at least 0.5 seconds may be predefined, and an exhalation of a complete and normal tidal volume breath may be predefined, and a sample will be collected from whichever breath occurs first. In a third variation, an apparatus may prompt or otherwise communicate with a user to interfere with the patient's breathing pattern such that the patient will produce a breath that meets a certain breath type. In a fourth variation, an apparatus may take an input of a physiological signal against which breath targeting thresholds may be set, in order to verify that a physiologically representative breath is targeted for the prevailing clinical conditions. In a fifth variation, an apparatus may target a physiologically representative breath if and when found, and if not found, will target a breath that is non-representative but will then apply a correction factor to normalize the result to a representative breath. In a sixth variation, the apparatus may prompt or communicate to the user to give the user the option of waiting for the pre-defined type of breath to occur, or to cancel the test to avoid long wait periods. In a seventh variation, the apparatus may require a targeted breath to both satisfy a breath type criteria and a breathing pattern stability criteria.

In an eight variation, an apparatus for analyzing a breath gas includes a sensor, a breath sampling system, a processor, and a gas analyzer. The sensor may measure a breathing pattern parameter. The breath sampling system may include a gas collection conduit. The processor may determine if an exhaled breath should be sampled for analysis based on a comparison of a breathing parameter threshold value to the measured breathing pattern parameter. The threshold value may delineate between a physiologically representative breath and a physiologically non-representative breath. The gas analyzer may analyze the breath gas.

In a ninth variation, an apparatus for analyzing a gas in exhaled breath includes a sensor, a breath sampling system, a processor, and a gas analyzer. The sensor may measure a breathing parameter including an expiratory signal. The breath sampling system may include a gas collection conduit. The processor may determine if an exhaled breath should be sampled for analysis based on a comparison of a breathing parameter threshold value to the measured expiratory breathing signal parameter, wherein the threshold value is a duration of a part of the breathing parameter. The gas analyzer may analyze the breath gas.

In a tenth variation, an apparatus for collection of and analysis of a gas in exhaled breath includes a sensor, a breath sampling system, a processor, and a gas analyzer. The sensor may measure a breathing parameter including an expiratory signal. The breath sampling system may include a gas collection conduit. The first processor may compare a breathing pattern threshold value to the measured breathing pattern parameter and determine if the measured parameter meets the threshold value, wherein the threshold value delineates between a physiologically representative breath and a physiologically non-representative breath. The gas analyzer may analyze the breath gas, wherein the gas analyzer comprises a second processor having a first gas analysis algorithm and a second gas analysis algorithm. The first gas analysis algorithm is used for breaths determined to meet the threshold value. The second gas analysis algorithm is used for breaths determined to not meet the threshold value, wherein the second algorithm comprises a correction factor to convert a non-representative result from a non-representative breath to a representative result.

In an eleventh variation, an apparatus for collection of and analysis of a gas in exhaled breath includes a sensor, a breath sampling system, a processor, and a gas analyzer. The sensor may measure a breathing parameter including an expiratory signal. The breath sampling system may include a gas collection conduit. The processor may include an input to receive a physiological signal, wherein the processor compares a breathing pattern parameter threshold value to the measured breathing pattern parameter and determines if a breath meets the threshold value, wherein the threshold value is defined based on the physiological signal, and wherein the threshold value is defined to delineate between a physiologically representative breath and a physiologically non-representative breath. The gas analyzer may analyze the breath gas.

In a twelfth variation, the threshold value in any one of eighth through eleventh variations is selected to be representative of a complete tidal volume breath.

In a thirteenth variation, the apparatus in any one of eighth through twelfth variations includes a breath signal trending algorithm, and wherein the threshold value is at least one selected from the group consisting of: a peak amplitude value, a baseline value, a time duration above the peak amplitude value, a time duration below the baseline value, and a percent comparison of a current breath to trending algorithm.

In a fourteenth variation, the threshold value in any one of eighth through thirteenth variations is selected to be an amplitude value and a baseline value, wherein the values are selected to represent a complete tidal volume breath.

In a fifteenth variation, the breath parameter threshold value of the tenth variation is a breath rate of less than or equal to 60 breaths per minute.

In a sixteenth variation, the threshold value in any one of eighth through fifteenth variations is based on at least one selected from the group consisting of an expiratory time, a portion of an expiratory time, an airway pressure, a $CO_2$ value (over time), an $O_2$ value (over time), an airway temperature, a breath flow rate, a breath rate, a depth of breath, a duration of breath, an inspiratory time, a pre-end-tidal time, an end-tidal time, a post-expiratory time, an inspiratory pause, a peak inspiratory pressure, a peak expiratory pressure, a characteristic waveform for sneeze, cough, stacked breath or non-full breath, an inspiratory amplitude, an expiratory amplitude, and a historical breath criteria.

In a seventeenth variation, the physiologic signal of the tenth variation is representative of a physiological parameter of a patient, wherein the physiological parameter is at least one selected from the group consisting of a blood pressure, a heart rate, chest impedance, a weight, a height, an age, a race, a sex, a diagnosis, a respiratory rate, a tidal volume, a minute volume, an inspiratory:expiratory ratio, a blood gas, a cardiac output, an end tidal $CO_2$ concentration, a pulmonary perfusion, a base excess, an $O_2$ sat, and a ventilation:perfusion ratio.

In an eighteenth variation, the processor in any one of eighth through seventeenth variations further comprises a breath type information algorithm to determine a breath for sampling, wherein the algorithm is at least partly based upon determining the breath is at least one selected from the group consisting of a breath hold, a deep breath, a forced exhaled breath, an inspiratory pause, an expiratory pause, a resting respiration, and a breath pattern repetition.

In a nineteenth variation, a breath trending algorithm of any one of eighth through eighteenth variations is at least partly based upon a breath pattern and wherein the algorithm determines to sample after a predetermined number of repetitive breaths.

In a twentieth variation, the predetermined number of breaths of the nineteenth variation is between 1 and 5 breaths.

In a twenty-first variation, the predetermined number of breaths of the nineteenth variation is between 2 and 4 breaths.

In a twenty-second variation, an apparatus for analyzing an exhaled breath includes a sensor, a first processor, and a breath sampling system. The sensor may measure a parameter of the exhaled breath. The first processor may determine if the measured parameter meets a predetermined criteria corresponding to a physiologically representative breath. The breath sampling system may store the exhaled breath when the first processor determines the measured parameter meets the predetermined criteria.

In a twenty-third variation, the apparatus of the twenty-second variation includes a gas analyzer to analyze the stored breath. In a twenty-fourth variation, the gas analyzer of the twenty-third variation includes a second processor that applies a first gas analysis algorithm when the first processor determines the measured parameter meets the predetermined criteria and applies a second gas analysis algorithm when the first processor determines the measured parameter does not meet the predetermined criteria, wherein the second algorithm comprises a correction factor.

In a twenty-fifth variation, the apparatus of any of the twenty-second through twenty-fourth variations includes a physiologic sensor that monitors a physiological parameter of a patient and wherein the breath sampling system does not store the exhaled breath when a third processor determines the physiological parameter does not meet a predetermined physiological criteria.

In a twenty-sixth variation, the physiologic parameter of the twenty-fifth variation includes at least one selected from the group consisting of a blood pressure, a heart rate, chest impedance, a weight, a height, an age, a race, a sex, a diagnosis, a respiratory rate, a tidal volume, a minute volume, an inspiratory:expiratory ratio, a blood gas, a cardiac output, an end tidal $CO_2$ concentration, a pulmonary perfusion, a base excess, an $O_2$ sat, and a ventilation:perfusion ratio.

In a twenty-seventh variation, the predetermined criteria of any of the twenty-second through twenty-sixth variations includes a minimum duration.

In a twenty-eight variation, the predetermined criteria of any of the twenty-second through twenty-seventh variations includes at least one selected from the group consisting of: a peak amplitude value, a baseline value, a time duration above the peak amplitude value, a time duration below the baseline value, and a percent comparison of a current breath to a trending algorithm.

In a twenty-ninth variation, the predetermined criteria of any of the twenty-second through twenty-eighth variations includes an amplitude value and a baseline value representing a complete tidal volume breath In a thirtieth variation, the predetermined criteria of any of the twenty-second through twenty-ninth variations includes a breath rate of less than or equal to 60 breaths per minute.

In a thirty-first variation, the predetermined criteria of any of the twenty-second through thirtieth variations is based on at least one selected from the group consisting of an expiratory time, a portion of an expiratory time, an airway pressure, a $CO_2$ value over time, an $O_2$ value over time, an airway temperature, a breath flow rate, a breath rate, a depth of breath, a duration of breath, an inspiratory time, a pre-end-tidal time, an end-tidal time, a post-expiratory time, an inspiratory pause, a peak inspiratory pressure, a peak expiratory pressure, a characteristic waveform for sneeze, cough, stacked breath or non-full breath, an inspiratory amplitude, an expiratory amplitude, and a historical breath criteria.

In a thirty-second variation, the predetermined criteria of any of the twenty-second through thirty-first variations is based upon at least one selected from the group consisting of a breath hold, a deep breath, a forced exhaled breath, an inspiratory pause, an expiratory pause, a resting respiration, and a breath pattern repetition.

In a thirty-third variation, the predetermined criteria of any of the twenty-second through thirty-first variations is based upon a predetermined number of repetitive breaths.

In a thirty-fourth variation, the number of repetitive breaths of the thirty-third variation is between 1 and 5 breaths.

In a thirty-fifth variation, the number of repetitive breaths of the thirty-fourth variation is between 2 and 4 breaths.

In a thirty-sixth variation, an apparatus for analyzing breath gas includes a sensor, a first processor, a second processor, a third processor, and a breath sampling system. The sensor may measure parameters of a first exhaled breath, a second exhaled breath, and a third exhaled breath. The first processor may determine if a first measurement of the first exhaled breath meets a first predetermined criteria. The second processor may determine if a second measurement of the second exhaled breath meets a second predetermined criteria, wherein the second measurement is made when the first measurement is determined to meet the first predetermined criteria. The third processor may determine if a third measurement of the third exhaled breath meets a third predetermined criteria, wherein the third measurement is made when the second measurement is determined to meet the second predetermined criteria. The breath sampling system may store the third exhaled breath when the third processor determines the third measured parameter meets the third predetermined criteria.

In a thirty-seventh variation, the third predetermined criteria of the thirty-sixth variation is based upon a trend associated with a plurality of breaths.

In a thirty-eight variation, a method for analyzing breath gas includes: measuring parameters of a first exhaled breath, a second exhaled breath, and a third exhaled breath; determining if a first measurement of the first exhaled breath meets a first predetermined criteria; determining if a second measurement of the second exhaled breath meets a second predetermined criteria, wherein the second measurement is made when the first measurement is determined to meet the first predetermined criteria; determining if a third measurement of the third exhaled breath meets a third predetermined criteria, wherein the third measurement is made when the second measurement is determined to meet the second predetermined criteria; and storing the third exhaled breath when the third measurement is determined to meet the third predetermined criteria.

In a thirty-ninth variation, the third predetermined criteria of the thirty-eight variation is based upon a trend associated with a plurality of breaths.

DETAILED DESCRIPTION

Described here are devices and methods for measuring certain breath waveform characteristics. The measured characteristics may be used to discriminate between breaths that may produce an accurate gas measurement and breaths that may not produce an accurate gas measurement. In the variations shown, for exemplary purposes, ETCO gas measurements are described, and the patient's breath sample is shown to be drawn into the instrument from the patient by application of vacuum. However the disclosure also applies to measurement of other breath gases and to other methods of collecting breath gas, such as patients breathing into an instrument for example.

In some variations, one or more breathing parameters may be measured to identify the different constituent portions of a breath and the respective time periods, and a pneumatic system may be used for capturing the portion of exhaled breath in a sampling tube using the identified time period. In some variations, one or more valves and/or flow control mechanisms, such as a vacuum pump for example, may be used to regulate the flow rate of gas drawn into the sampling tube. In some variations, the captured portion of breath may be analyzed for indications of a patient's physiological state.

Measured breathing parameters may include one or more of carbon dioxide, oxygen, airway pressure, airway temperature, breath flow rate, chest impedance, diaphragmatic movement or innervation, breath sounds, and breath vibrations. Identifying the time period of a portion of a breath may include identifying substantially the start and termination of that time period.

A diagnostic gas sample may be taken from the end-tidal period, for example when attempting to monitor a physiologic condition in the blood stream, such as hemolysis. For explanatory purposes, exemplary variations for sampling end-tidal gas for end-tidal CO measurement are given below, however the principles apply to other diagnostic purposes.

Figure 1:
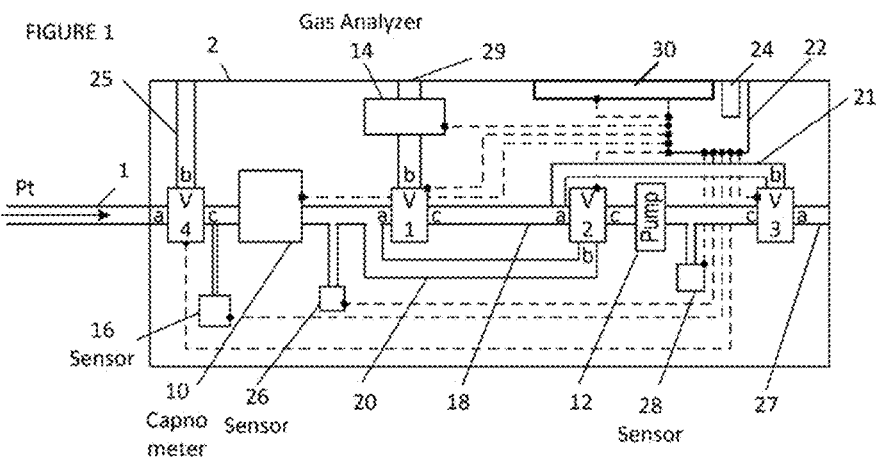
FIG. 1 describes schematically an overview of a breath analyzer in accordance with one variation.

FIG. 1 describes schematically an overview of one variation of a device for capturing exhaled breath, including a sampling cannula 1 and a gas sample collection and analysis instrument 2, in accordance with one variation. Gas may be drawn from the patient, for example using a sampling cannula 1 and a flow generator 12. The flow rate of the flow generator may be measured by a flow transducer, for example a pressure sensor array, 26 and 28, arranged like a pneumotach. The measured flow rate may be used as a closed loop feedback control to control the flow generator flow rate. A breath sensor, such as a capnometer 10 or a pressure sensor 26, is used to measure the breathing pattern in real time. Gas from the desired portion of the breath is captured and isolated in the storage collection compartment 18. Gas entering the storage compartment is controlled by at least one valve V1, for example with a common port c always open, and a second open port, either a to collect gas or b to isolate the storage compartment. There may be a valve V2 between V1 and the flow generator to participate with V1 in isolating the storage compartment. Gas not being captured for analysis is channeled away from the storage compartment via a bypass conduit 20. The captured gas is sent from the storage compartment through a gas composition analyzer 14, such as a CO sensor. A control system 22 with a microprocessor 24 controls the system with the associated algorithms. The flow generator for example can be a vacuum or pressure pump, such as a diaphragm pump, or another type of flow generating device such as a vacuum source, a Venturi from a positive pressure source, or a syringe pump. Valves to manage gas routing can be an arrangement of 3 way 2 position valves as shown, or can be an arrangement of 4-way 3-position valves. Capnometer 10, if used, measures the breathing pattern instantaneously using infrared (IR). The gas composition analyzer for example can be an electrochemical sensor with a reaction time, or a gas chromatographer, or a mass spectrometer. Other variations may use different gas analyzers. The sample storage compartment can be a small bore inner diameter tube or conduit of considerable length in order to reduce the cross section which reduces gas molecule interaction along the length of the conduit. The sampling cannula may be constructed of any non-rigid kink-resistant plastic, such as a thermoset plastic for example silicone, urethane or urethane blends, or such as a thermoplastic for example PVC, C-FLEX, or other materials. The cannula can have a range of inner diameters, and in some variations the cannula has a diameter of less than 0.080 inches in order for the breath gas to conform to columnar behavior with boundaries between breath sections where mixing across sections may be reduced.

Pressure sensor 16 is an additional pressure sensor that may be used in tandem with 26 so that a flow rate can be determined, in addition to using it for airway pressure measurement. Flow rate can be used to adjust the pump speed in some variations that utilize a variable flow rate. Pressure sensor 16 can also be utilized for ambient information where the breathing curve is measured by pressure instead of capnometry. In some variations, an instantaneous carbon monoxide sensor may be used as the breath sensor, in place of a capnometer or an airway pressure sensor. Other instantaneous breath sensors may also be used.

The bypass tube 20 allows the gas being drawn from the patient or from ambient to bypass the sample tube 18 during times which the sample tube may be isolated from these gases. In this arrangement, valve V1 may be closed at port a and valve V2 may be open at port b to allow flow from b through c. A flow generator may be used to draw the sampling gas through the bypass type. A push tube 21 may be used to push the end-tidal sample in the sample tube 18 out of the sample tube to the sensor 14, at which time valves V1 and V3 are each open at port b and V2 is closed at port a. Valve V4 switches the source gas from patient gas to ambient gas by opening port b, when it is desired to not contaminate the internal gas pathways with patient gas or for purging the system.

Figure 1B:
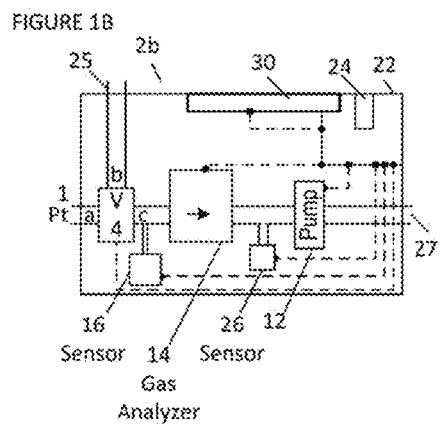
FIG. 1b schematically describes an optional overview of the breath analyzer in which the analysis may be conducted in substantially real time, in accordance with one variation.
Figure 1C:
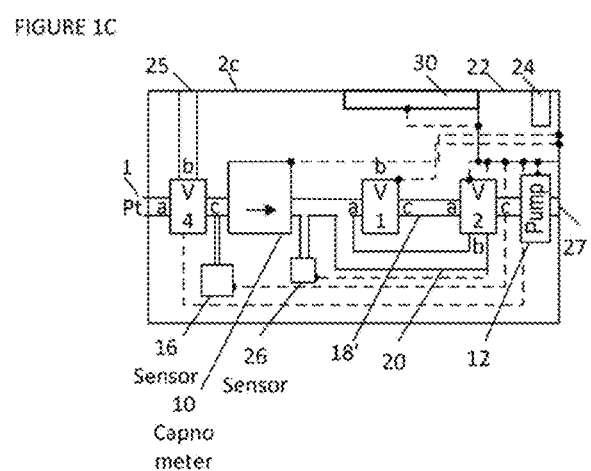
FIG. 1c schematically describes an optional overview of the breath analyzer in which the sample may be saved and the analysis may be conducted at a later time, in accordance with one variation.

In some variations, the pneumatic system shown in FIG. 1 above may include a removable sampling compartment 18' as shown by the instrument 2c in FIG. 1c. For example, sample tube 18' may be removable from the system. In this way, the pneumatic system may be able to fill a sample tube with a desired gas, and the sample tube may be analyzed at another location, or preserved for later analysis. In other variations, the gas may be routed from the sample tube to a removable sampling compartment. In this variation, the compartment may replace the analyzer 14 or otherwise be positioned so that it can be removed and/or replaced. In other variations, exemplified in FIG. 1b, the analyte in question may be measured by the instrument 2b in real time or substantially real time by the sensor 14. In this case, the sensor 14 may be responsible for measuring the breathing signal for the purposes of breath selection and determination of the section of the selected breath that should be measured, as well as for measuring the level of the analyte in question. Or, optionally, the sensor 16 may be responsible for breath selection and breath section targeting, while the sensor 14 is responsible for measuring the level of the analyte in question. In any case, the breath selection algorithms and the breath section targeting algorithms described throughout apply to all of the different types of instrument configurations.

Figure 2:
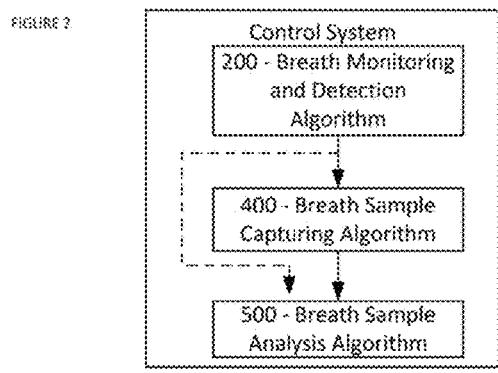
FIG. 2 describes an exemplary control system for operating the breath analyzer of FIG. 1, in accordance with one variation.

FIG. 2 describes an exemplary control system 22 for operating the device of FIG. 1, in accordance with one variation. One module or algorithm 200 performs the breath monitoring and detection function. In this module, a determination is made if the breathing pattern or individual breaths meet certain criteria, in order to determine whether or not a breath will be captured for analysis. In some variations, the criteria may be predefined, or defined in real-time, or user-defined, automatically defined or semi-automatically defined. For example, predefined criteria may be absolute or relative threshold parameters stored in the device's software. Or a user may enter certain information relative to the specific test being performed, and the system may use that information to define the criteria. Or the system can automatically establish the criteria in real time based on the prevailing conditions. Or a combination of the above techniques can be employed. A subsequent control system, module, or algorithm 400 performs the breath sample capturing function, and another subsequent control system, module, or algorithm 500 performs the breath sample analysis. As shown by the dashed line in FIG. 2, an alternative sequence of operation is contemplated in which the breath sample capturing algorithm 400 is skipped for those instrument configurations in which the sample analysis step 500 is performed in real time or substantially real time.

Figure 3:
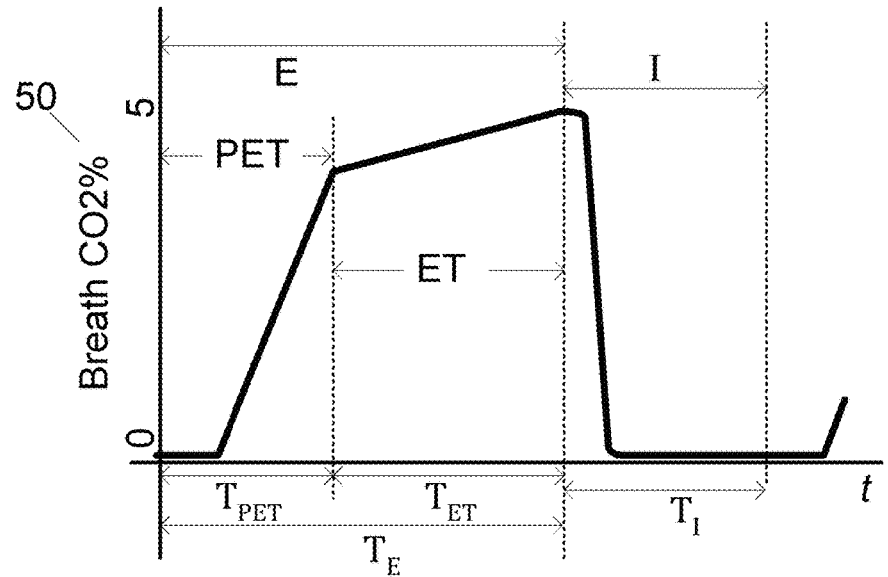
FIG. 3 graphically describes a typical breath monitoring waveform based on a carbon dioxide measurement which is taken on gas being drawn from a breath, in accordance with one variation.
Figure 4:
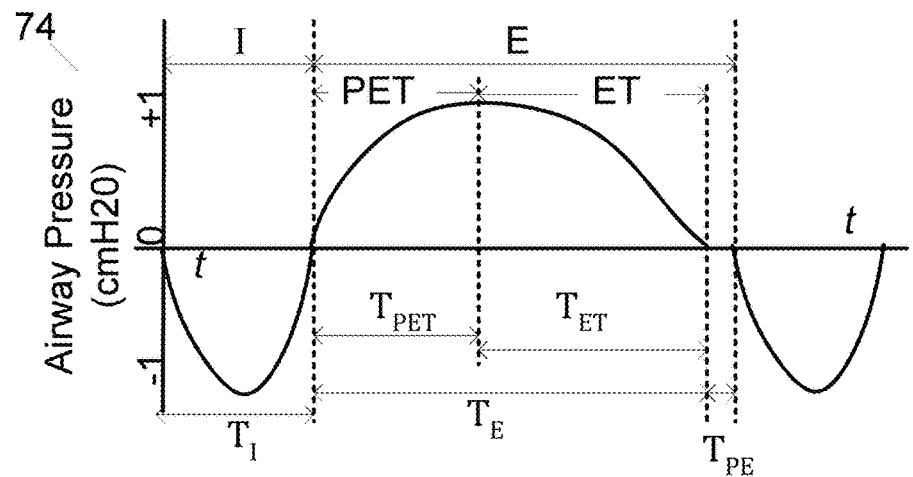
FIG. 4 graphically describes a typical breath monitoring waveform based on an airway pressure measurement taken at the proximal airway, in accordance with one variation.

FIGS. 3 and 4 describe a typical breathing signal pattern of a breath based on $CO_2$ and airway pressure respectively. FIG. 3 graphically describes a typical breathing pattern from the perspective of a carbon dioxide ($CO_2$) signal measured in breath drawn from the person's airway, such as from their nose, as a function of time, with time on the horizontal axis, and $CO_2$ level on the vertical axis, in accordance with one variation. During the expiratory phase E, $CO_2$ is expelled, hence the $CO_2$ level increases. During the inspiratory phase I, ambient air occupies the nose, hence the measured $CO_2$ drops to essentially zero. There may be a variety of shapes to a breath $CO_2$ curve, based on the person's breathing pattern, their age, how they are breathing and any underlying acute or chronic medical conditions. A curve may show the following sub-portions for the expiratory phase: (1) a beginning portion or pre-end-tidal section PET, comprising low $CO_2$ because the gas may simply be gas from the proximal airway devoid of $CO_2$, (2) a middle portion showing $CO_2$ rapidly increasing from zero to the $CO_2$ level at the distal segments of the lungs, and (3) an end-tidal ET portion showing a plateauing or leveling off of the $CO_2$, representing the $CO_2$ coming from the alveoli for that exhaled breath, and (4) potentially a constant peak level at the very end of the expiratory period. However, there can be many other curves different from this curve. Peak $CO_2$ levels are typically 4-6% during the end-tidal period and close to or equal to zero during the inspiratory period.

In some variations, the level of $CO_2$ in an exhaled breath may be used to determine the duration of a period of a breath, such as the pre-end-tidal time TPET, expiratory time TE, end-tidal time TET, inspiratory time T1, or breath period time TBP. In further variations, a duration of a period of breath may be characterized by a start and a termination of that period. In some variations, a $CO_2$ level may be used to determine a start or a termination of a period of a breath. In other variations, a first time derivative of a $CO_2$ level may be used to determine a start or a termination of a period of a breath. In yet other variations, a second time derivative of a $CO_2$ level may be used to determine a start or a termination of a period of a breath. In some variations, a combination of $CO_2$ levels and $CO_2$ level time derivatives may be used to determine a start or a termination of a period of a breath. In some variations, a start of an end-tidal period may be determined by a change in the first time derivative of a $CO_2$ level of the exhaled breath, such as a sudden decrease in the first time derivative of the $CO_2$ level. In some variations, a decrease in the first time derivate of the $CO_2$ level may be more than a 10% decrease. In some variations, a decrease in the first time derivate of the $CO_2$ level may be more than a 25% decrease. In some variations, the derivative will approach or become zero showing very little rate of change or a peak plateau respectively. In other variations, the start of an end-tidal period may be determined by a large second time derivative of the $CO_2$ level. In some variations, a termination of an end-tidal period may be determined by a maximum $CO_2$ level, which may be detected or confirmed by a change in the sign of the first time derivative of the $CO_2$ level as the derivative becomes negative associated with a drop of the $CO_2$ level from its peak value. In further variations, a start of a beginning period may be determined by a sudden increase in the first time derivative of the $CO_2$ level. In other variations, the start of a beginning period may be determined by an increase in the $CO_2$ level from zero $CO_2$ level. In some variations, a termination of a middle period may be determined by a change in the first time derivative of a $CO_2$ level of the exhaled breath, such as a sudden decrease in the first time derivative of the $CO_2$ level. In some variations, a $CO_2$ level, first time derivative thereof, or second time derivative thereof may be used to determine the start and termination of one or more periods. Other breath-borne gases may be used in place of $CO_2$ for measuring the breathing curve. For example, oxygen can be measured which would indicate a higher oxygen concentration during inspiration than expiration. It is also contemplated that the breathing pattern may be instantaneously or substantially instantaneously measured by a fast-responding CO sensor. In this case referring to FIG. 1, the sensor 10 may be a fast responding CO sensor that depicts the breathing pattern and also measures the end-tidal CO level. After application of the various breath qualification and disqualification variations described subsequently, the CO level of a qualified breath can be reported as the result.

FIG. 4 graphically describes a typical breathing signal from the perspective of measured airway pressure, showing a negative pressure during inspiratory phase and a positive pressure during expiratory phase, in accordance with one variation. Typically during at rest breathing the peak expiratory pressure may correspond to the middle of the expiratory phase and the start of the end-tidal period. In FIGS. 3 and 4, TI, TE, TPET, TET, TPE represent inspiratory time, expiratory time, pre-end-tidal time, end-tidal time, and post expiratory time respectively. An inspiratory pause may also be present (not shown), in which the peak of lung muscle movement during inspiration is paused before the expiratory period begins. Peak inspiratory pressure may be −1 to −4 cwp during restful breathing, and up to −15 cwp during heavier breathing, and peak expiratory pressure may be +0.5 to +2.0 cwp during restful breathing and up to +10 cwp during heavier breathing when measured at the entrance to the nostrils. Representative pressures and gas concentrations may vary with environmental conditions, for example airway pressures during cold temperatures may be increased for the same unit of volume.

In some variations, airway pressure may be used to determine a start or a termination of a period of a breath. In other variations, a first time derivative of an airway pressure may be used to determine a start or a termination of a period of a breath. In yet other variations, a second time derivative of an airway pressure may be used to determine a start or a termination of a period of a breath. In some variations, a combination of airway pressures and airway pressure time derivatives may be used to determine a start or a termination of a period of a breath. In some variations, a start of an end-tidal period may be determined by maximum airway pressure, that is, by a zero first time derivative of the airway pressure. In some variations, a termination of an end-tidal period may be determined by zero airway pressure. In some variations, an airway pressure, first time derivative thereof, or second time derivative thereof may be used to determine the start and termination of one or more periods. Airway pressure may be measured through a secondary lumen extending the length of the cannula in parallel with the sampling lumen, or may be measured by teeing into the sampling lumen, or by placing a sensing transducer at the airway of the patient.

In some variations, a breath sensor monitors the person's breathing over time, and trends the breathing pattern by determining a continually updated value that is characteristic of the breathing pattern. For example, peak positive values of a breathing signal may be measured and updated for each breath. Peak values may be compared with previous peak values. Peak values may be averaged over a previous number of multiple breaths. Similarly, time-related aspects of the breaths may be trended, such as the expiratory time. Various breath-related events that are not normal breaths may be identified and exception algorithms may exist in order to not include these non-normal breath events inadvertently in deterministic steps. For example, the characteristic waveform of a sneeze, cough, stacked breath, or non-full breath may be defined in advance or based on monitoring of a particular patient, and when detected by the breathing sensor, excepted from the appropriate deterministic algorithms.

Figure 5:
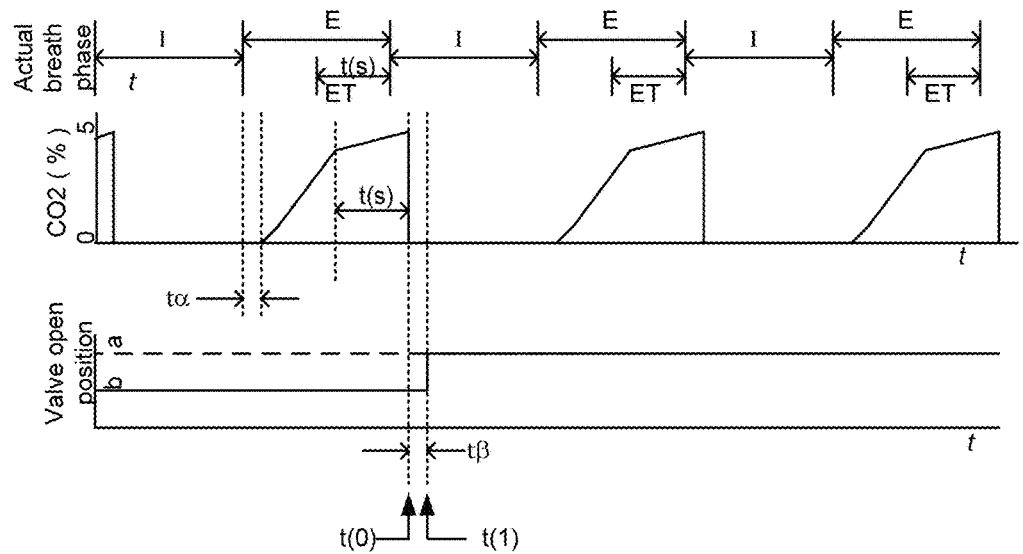
FIG. 5 is a timing diagram describing the sequence of operation of capturing a gas sample based on capnometry, in accordance with one variation.

FIG. 5 graphically describes a lag period between when the gas sample exits a breath sensor and when the sample reaches the sample tube, in accordance with one variation. The top tracing shows the actual breath phases as a function of time for three breaths, the middle tracing shows a capnometry signal versus time for the sequence of breaths and the lag period between when the gas sample exits the capnometer and reaches the sample tube input valve. The travel time for gas to travel from the person to the capnometer through the sampling cannula is represented by tα. Therefore the capnometry signal shows a beginning of exhalation slightly after the true beginning of exhalation. The travel time for the gas to exit the capnometer and begin to enter the sample collection compartment is represented by tβ. Therefore, as shown in the bottom tracing, the sample compartment isolation valve V1 is open to position a at time t(1), tβ after detection of the start of the end-tidal period by the capnometer, for the sample collection time t(s).

Figure 6:
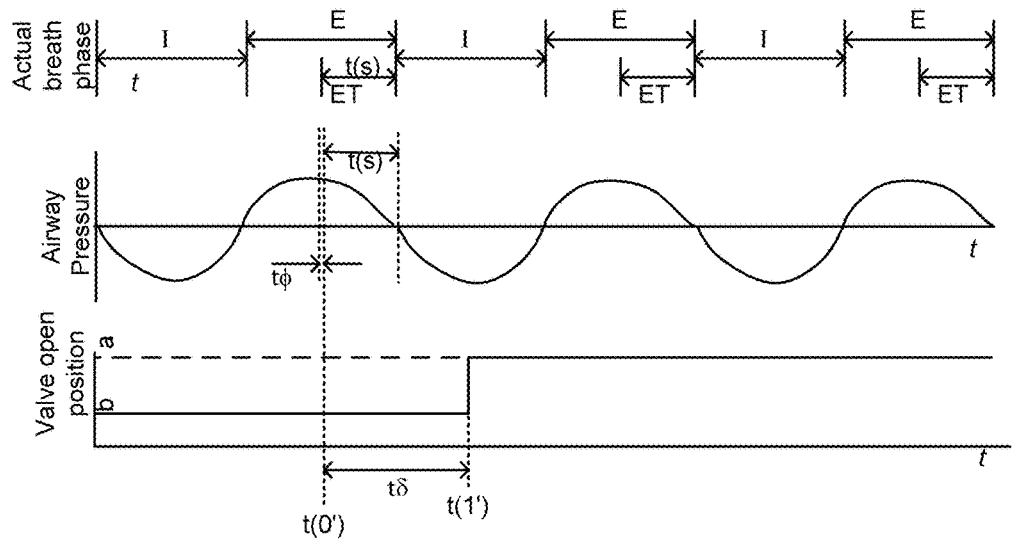
FIG. 6 is a timing diagram describing the sequence of operation of capturing the gas sample based on airway pressure monitoring, in accordance with one variation.

FIG. 6 graphically describes an airway pressure signal versus time for a sequence of breaths, in accordance with one variation. The top tracing shows the actual breath phases, the middle tracing shows the airway pressure signal and the lower tracing shows the sample isolation tube valve V1 position. In airway pressure tracing the lag period between the gas sample leaving the patient's airway and reaching the sample tube input valve is shown. The phase shift between the actual breath, and the pressure is tφ, approximately equal to the distance of travel divided by the speed of sound, hence is relatively instantaneous. The travel time for the gas to exit the person's airway and begin to enter the sample collection compartment is represented by tδ, Therefore the valve V1 opens to position a at time t(1'), tδ after detection of the start of the end-tidal period by the capnometer, for the sample collection time t(s). Capnometry and airway pressure signals are shown in FIGS. 5 and 6 for exemplary reasons, and the breathing sensor may be of other times, such as temperature or acoustic.

Figure 8:
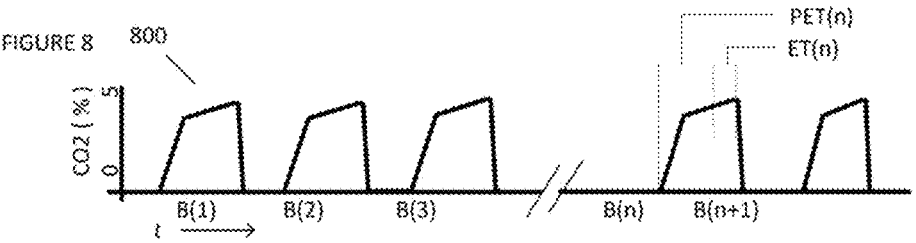
FIG. 8 graphically describes a capnometry signal versus time for a sequence of breaths from which a sample is taken, in accordance with one variation.

FIG. 8 graphically describes breath waveforms 800 versus time for a series of breaths B(1), B(2) to B(n+1) being monitored by the system 2, in accordance with one variation. In the example shown, the breathing signal is a Capnometry signal, however it could be any other breath sensor signal. Eventually the system 2 determines that a specific breath, or number of breaths, or the breathing pattern meets the necessary criteria and a breath or a number of breaths is/are targeted for capturing gas from the end-tidal section of that breath or breaths. In the example shown, the end-tidal sample ET(n) of breath B(n) is targeted for sample acquisition and compositional measurement.

Figure 7:
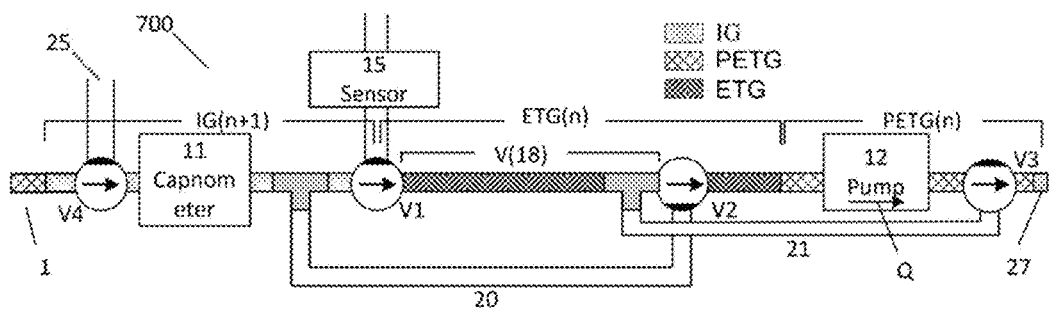
FIG. 7 is a pneumatic schematic describing the capturing of a sample from the series of breaths described in FIG. 8, in accordance with one variation.

FIG. 7 describes the pneumatic system 700 and exemplary operation of the system 2 shown in FIG. 1, in accordance with one variation. In FIG. 7, a volume V(18) the end-tidal gas from breath B(n) in FIG. 8 is transported by the system 700 into the sample compartment 18 where it is captured and isolated from other gases, prior to analysis by the sensor 15. The flow path of the patient gas prior to capturing the sample is from the patient through V4, the Capnometer 11, V1, the sample tube 18, V2, the pump 12, V3, then out the exhaust 27. When the tail end of the end-tidal sample reaches V1 or the entrance to the sample tube 18, the valves switch such that the flow path is from the ambient inlet 25, through V4, the Capnometer 11, the bypass tube 20, V2, the pump 12, then out the exhaust 27. When the system is ready to send the sample from the sample tube to the sensor 15, the valves are switched such that the flow path is changed from the patient inlet 1 to the ambient inlet 25, through V4, the Capnometer 11, the bypass tube 20, V2, the pump 12, the push tube 21, the sample tube 18, V1, then through the sensor 15 and out the sensor exhaust. The push tube is purged of any patient gas prior to these maneuvers.

Figure 9:
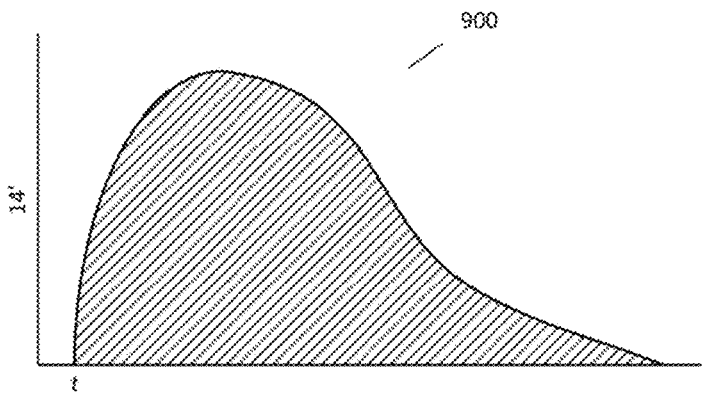
FIG. 9 is a graph of signal strength versus time, in accordance with one variation.

FIG. 9 shows a portion of a graph 900 of sensor signal strength versus time, in accordance with one variation. The sensor may include sensor 15, discussed above. In the example shown, the signal 14' is a voltage or current response from a reaction taking place in an electrochemical sensor. As the sample is sent through the sensor, the sensor reacts accordingly by a signal rise. The rise and duration are related to the amount of gas in the sample. Integrating the sensor signal over time, or averaging the sensor signal over time, will provide a correlation to the amount of gas in the sample. In some variations, system calibration may improve accuracy. It is contemplated by the invention that the timing and location of the analysis of the analyte in question may be performed a number of ways. For example, the analysis may be in real time or substantially real time as the exhaled breath is being drawn or obtained from the subject. Or, the analysis may be performed at some later time by saving the captured sample. Or, as shown in some of the embodiments for exemplary purposes, the analysis may be performed a short time after sample acquisition by the same instrument. In some of these cases, aspects of the apparatus shown in FIG. 7 are not required, however the breath selection algorithms required to measure a physiologically representative breath, described throughout, still apply. For example, a sample tube 18 to isolate and hold the sample may not be required, and bypass tube 20 and push tube 21 may not be required. Or the sensor 14 may not be required as the sensor 10 may measure both the breathing signal for determining and selecting a representative breath, as well as measures the level of the analyte in question. In addition, some of the Valves V1 through V4 may not be required. Or, for example, the breath sample acquisition instrument may be coupled to another analyte measuring instrument, such as a gas chromatograph or other analytical instrument, The foregoing examples are offered for illustration purposes and should not be construed to limit the disclosure.

Figure 10:
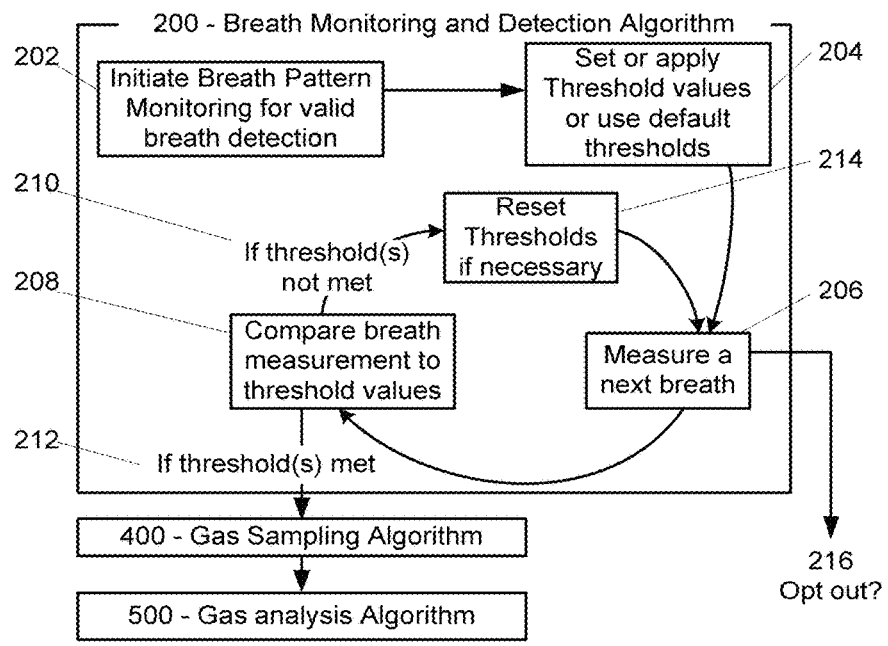
FIG. 10 describes a flow chart of a variation of a breath detection and monitoring method in which measured breath values are compared against set thresholds, in accordance with one variation.

FIG. 10 describes a flow diagram of a variation of a breath monitoring and detection algorithm 200 in which measured breath values, for example, gas concentration, are compared against set thresholds, in accordance with one variation. In Step 202, the breathing pattern monitoring in search of a desired breath is initiated. In Step 204, threshold values or criteria are applied to which the measured breathing signal will be compared. In Step 206 a next breath is measured. In Step 208 the measured breath is compared to the threshold values or criteria set in Step 204. In Steps 210 and 212, a determination is made whether the thresholds are not met or met respectively. If met, the system transitions to the gas sampling algorithm 400. If not met, the system may reset the threshold values or criteria in Step 214 and then measure a next breath. At any time if the criteria are not being met, the system may provide an option to cancel or opt out of the testing in Step 216. In some variations, the thresholds may be factory defaults, or selected from a menu of defaults corresponding to different clinical situations. The thresholds may be determined by the user, or by the system based on information related to the test that is inputted by the user. In some variations, the thresholds may be applied to an expiratory signal or an inspiratory signal, and may include amplitude criteria, timing criteria, timing criteria required to meet an amplitude criteria, amplitude criteria required to meet a timing criteria, averaging criteria, percentage criteria, and any combination thereof. As the system monitors the patient's breathing pattern, the threshold values may be updated as necessary. Once the threshold values are met, the system moves on to the sampling and analysis algorithms 400 and 500 respectively.

Figure 11:
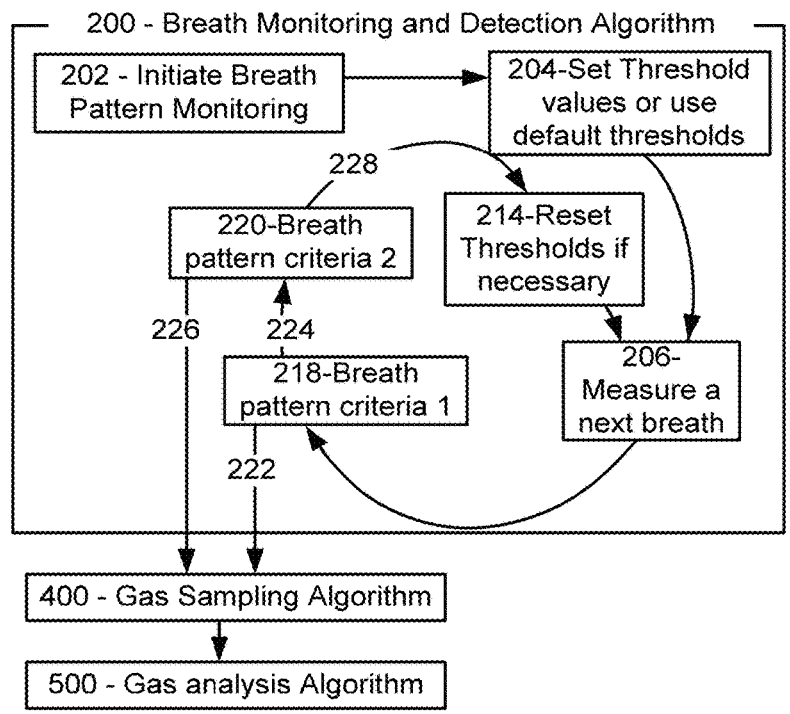
FIG. 11 describes a flow chart of a variation of a breath detection and monitoring method in which measured breath values are compared against a second set of criteria if a first set is not met, in accordance with one variation.

FIG. 11 describes a flow chart of a variation of a breath monitoring and detection algorithm 200 in which a measured breath value can be compared against a second set of criteria if a first set is not met, in accordance with one variation. For example, after initiating the breathing monitoring in Step 202, in Step 204 a first criteria may be set and may be a simple criteria such as a breath rate requirement, for example, 20-40 breaths per minute. After measuring a breath in Step 206 and applying the criteria in Step 218, if that criteria is met as determined in Step 222, the system enters the gas sampling algorithm Step 400. If however that first criteria is not met as determined in Step 224, the system applies a second, more complex set of criteria in Step 220. This second set of criteria might be multiple criteria, for example the combination of an amplitude criteria, a timing criteria, and a percentage of historical breath average criteria. Once the second set of criteria are met, for example as determined in Step 226, the system may enter the gas sampling algorithm Step 400. The gas sampling algorithm and gas analysis algorithm may factor in which of the first or second criteria was met. For example, one criteria may indicate a more consistent sample than another, and the algorithms may adjust accordingly. In some variations, third, fourth, fifth, or any number of criteria may be used and the sampling and analysis algorithms adjust according to the criteria which was met by the sample. In some variations, as shown in Step 214, the first or second set of criteria may be adjusted, updated, reset or changed, for example based on the prevailing conditions.

Figure 12:
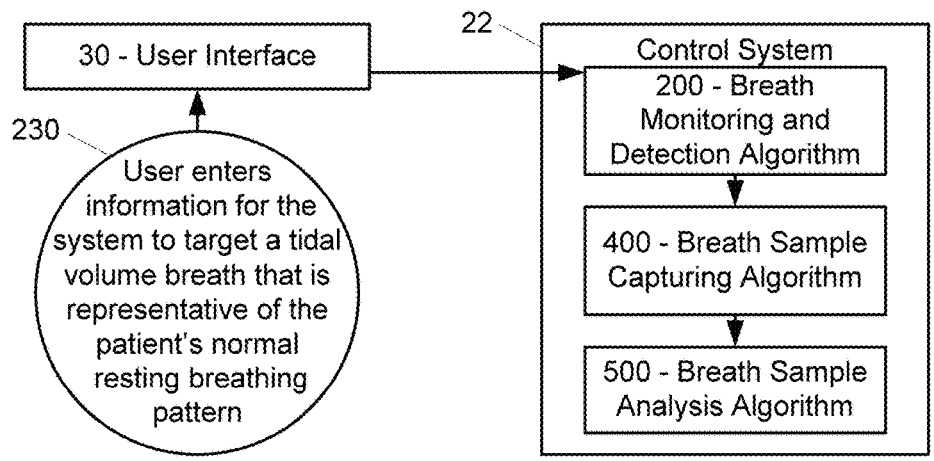
FIG. 12 describes a flow chart of one variation in which a user can enter clinical information into the system so that the system can delineate between representative and non-representative breaths for the diagnostic test being undertaken, in accordance with one variation.
Figure 13:
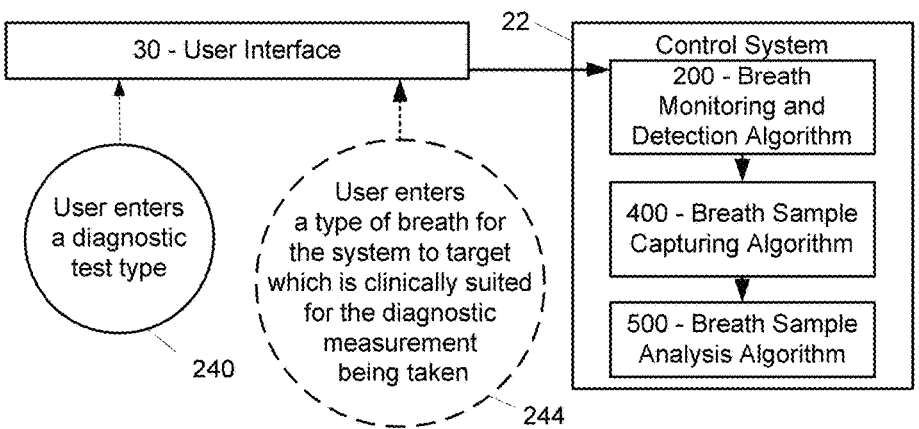
FIG. 13 describes a flow chart of one variation in which a user can enter breath type information into the system so that the system can delineate between representative and non-representative breaths for the diagnostic test being undertaken, in accordance with one variation.
Figure 14:
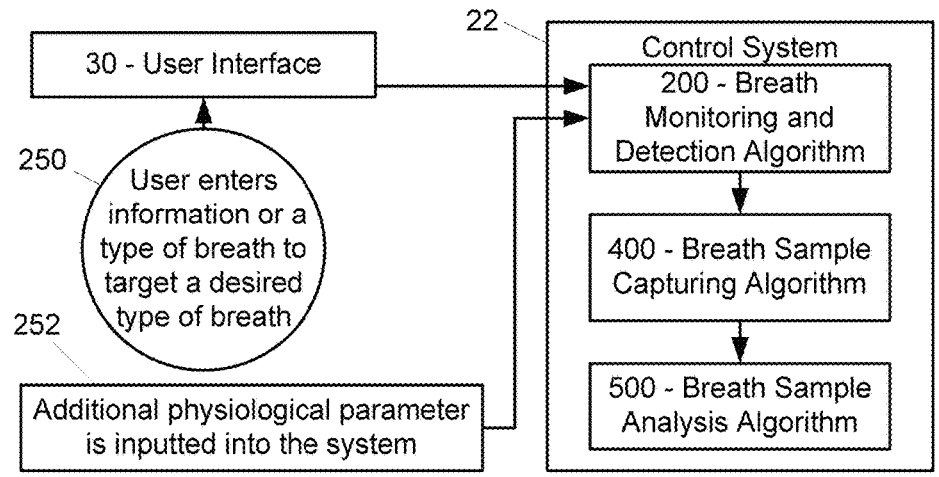
FIG. 14 describes a flow chart of one variation in which a system receives a physiological signal input from a secondary monitor so that the system can calibrate its algorithms to a physiological parameter of the patient, in accordance with one variation.

FIGS. 12 through 14 describe algorithms which calibrate the system to look for and target physiologically representative breaths that can yield desired results for the given clinical situation. Once the system is calibrated with relevant input parameters, the system searches for the appropriate type of breath and may dismiss other breaths. Once the appropriate type of breath is found, the system may capture and analyze the end-tidal portion of that breath. The subsequent breath analysis step therefore will provide an accurate correlation to the underlying disease. For example, if ETCO is being measured, breaths during hyperventilation may be categorized as non-representative breaths and may be dismissed. Or breaths during deep forced breathing may likewise be categorized as non-representative breaths and may be dismissed. Without these algorithms, a non-representative breath may be captured and analyzed, yielding a result that may not truly correlate to the blood level or to the underlying disease.

FIG. 12 describes a flow diagram of one variation in which a user can enter relevant clinical information into the system's user interface 30 in Step 230, in accordance with one variation. The input may be used by the system's control system 22 to calibrate the breath monitoring and detection algorithms 200 in order to delineate between clinically representative and non-representative breaths relevant to the diagnostic test being undertaken. For example, the information entered can be age, weight, height, BMI, metabolic rate, sex, race, diagnosis, minute volume, tidal volume, respiratory rate, resting respiratory rate, inspiratory time, expiratory time, I:E ratio, heart rate, blood gases, or cardiac output, or combinations thereof. For example, if the age and weight of a neonate is entered, the breath detection algorithms may be calibrated to look for breaths that meet a certain breath rate. For example, if one day old and 7.5 lbs is entered, a breath rate of 55-65 may be assigned to the breath detection threshold parameters such that a breath typical of that patient's normal resting tidal volume breathing pattern is targeted, captured and analyzed.

FIG. 13 describes a flow diagram of one variation in which the user can enter desired breath type information into the system's user interface 30 in Step 244, in accordance with one variation. This input may be used by the system's control system 22 to calibrate the breath monitoring and detection algorithms 200 in order to delineate between representative and non-representative breaths for the diagnostic test being undertaken. For example, the breath type information entered can be a sigh breath, breath hold, deep breath, forced exhaled breath, inspiratory pause, or expiratory pause, breath rate or a breath frequency parameter, or combinations thereof. For example, when diagnosing a metabolic disorder, a qualitative analysis of the breath may be required to determine the presence or absence of a chemical. In this case, a deep breath and a breath hold maneuver may be an optimal breath for the qualitative measurement. Or for example, the clinician may determine the normal resting tidal volume breath rate of the patient, and enter this breath rate into the system which calibrates the breath monitoring and detection algorithms to this breath rate. For example, the breath rate entered may be 32 bpm, resulting in the algorithm thresholds to be set to 30-34 bpm, causing the system to search for, capture and analyze the end-tidal gas from a breath that meets that criteria. Alternatively, as shown by Step 240, the user may enter into the system's user interface 30 the type of diagnostic test to be performed, and with that information, and optionally in conjunction with the information entered in Step 244, the control system sets or selects the criteria for a desired breath to be used in the breath monitoring and detection algorithm 200.

FIG. 14 describes a flow diagram of one variation in which the system's control system 22 receives a physiological signal input from a secondary monitor in Step 252, in accordance with one variation. The input may be used by the system's control system to calibrate its breath monitoring and detection algorithms 200 to a physiological parameter of the patient, in order to delineate between representative and non-representative breaths for the diagnostic test being undertaken. For example the physiologic parameter may be heart rate, respiratory rate, etCO$_2$, blood pressure, cardiac output, pulmonary perfusion, blood gases, base excess, blood pressure, oxygen saturation, ventilation:perfusion ratio, or combinations thereof. For example, when measuring a certain chemical or analyte in the alveolar gas that diffuses from the blood stream, the diffusion rate from the blood into the alveoli may be dependent on the rate of pulmonary blood flow. The higher the heart rate or cardiac output, the higher the rate of diffusion and the higher concentration of the chemical in the alveolar gas. Therefore, once the cardiac output or heart rate is inputted into the system, the system can calibrate itself to those parameters to normalize the alveolar gas measurement result against the prevailing clinical conditions of the patient. In addition to the input of a physiological parameter, as shown in Step 250 a user may input into the user interface 30 a desired breath type to sample, or a desired diagnostic test to be performed, or a patient-related parameter, in order to complement the physiological parameter input from Step 252 in the breath monitoring and detection algorithm 200, so that the desired breath and or test is sampled and performed.

Figure 15:
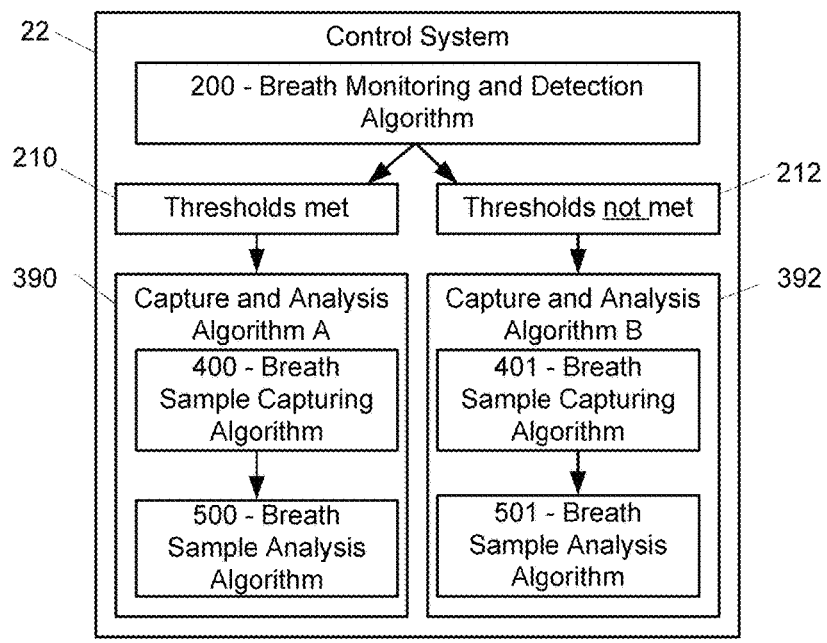
FIG. 15 describes a flow chart of a variation of a control system in which a secondary Capture and Analysis Algorithm may be used if the preferred breathing pattern threshold parameters are not met, in accordance with one variation.

FIG. 15 describes a flow diagram of a variation of a control system 22 in which a secondary capture and analysis algorithm B, 392, may be used if the primary or preferred breathing pattern threshold parameters are not met as determined in Step 212, in accordance with one variation. For example, a primary set of threshold parameters may be breath rate and expiratory time related parameters. For example, the Algorithm A, 390, may target an end-tidal section of gas from a breath that is physiologically representative of the normal breathing pattern, or resting tidal volume, or alternatively representative of the breath desired for the diagnostic application. If the primary set of threshold parameters are met as determined in Step 210, the system enters the capturing and analysis algorithms 400 and 500 respectively and determines a result accordingly. However, if these parameters are not met as determined in Step 212, the system may enter a second set of capture and analysis algorithms 401 and 501 respectively in Algorithm B, 392. For example, if the respiratory rate is too high and/or if the expiratory time is too short, the system's capture and analysis algorithms may include breath frequency correction. For example, the capturing subroutine 401 may result in a sample tube that may be 90% filled with end-tidal gas and 10% filled with pre-end-tidal gas, thus diluting the end-tidal sample. In this case the analysis algorithms 501 may mathematically correct for this dilution. Respiratory frequency and dilution are provided as one example in which a second set of algorithms may be required, however, it should be noted that there are other reasons that a second set of capture and analysis algorithms may be required. For example, Algorithm B may include receiving additional input from the user or automatically in order to calibrate the breath detection threshold parameters to the prevailing clinical situation. For example, if the patient is hyperventilating, it may be predetermined that the end-tidal gas measurement is for example 50% of a true measurement, and the system may capture, analyze and adjust as necessary. Other potential input parameters may be a heart parameter such as heart rate, cardiac output or blood flow, a gas exchange parameter such as blood gases or pulse oximetry, other respiratory parameters such as minute volume, or a patient type parameter such as age, sex, height or disease state.

Figure 16:
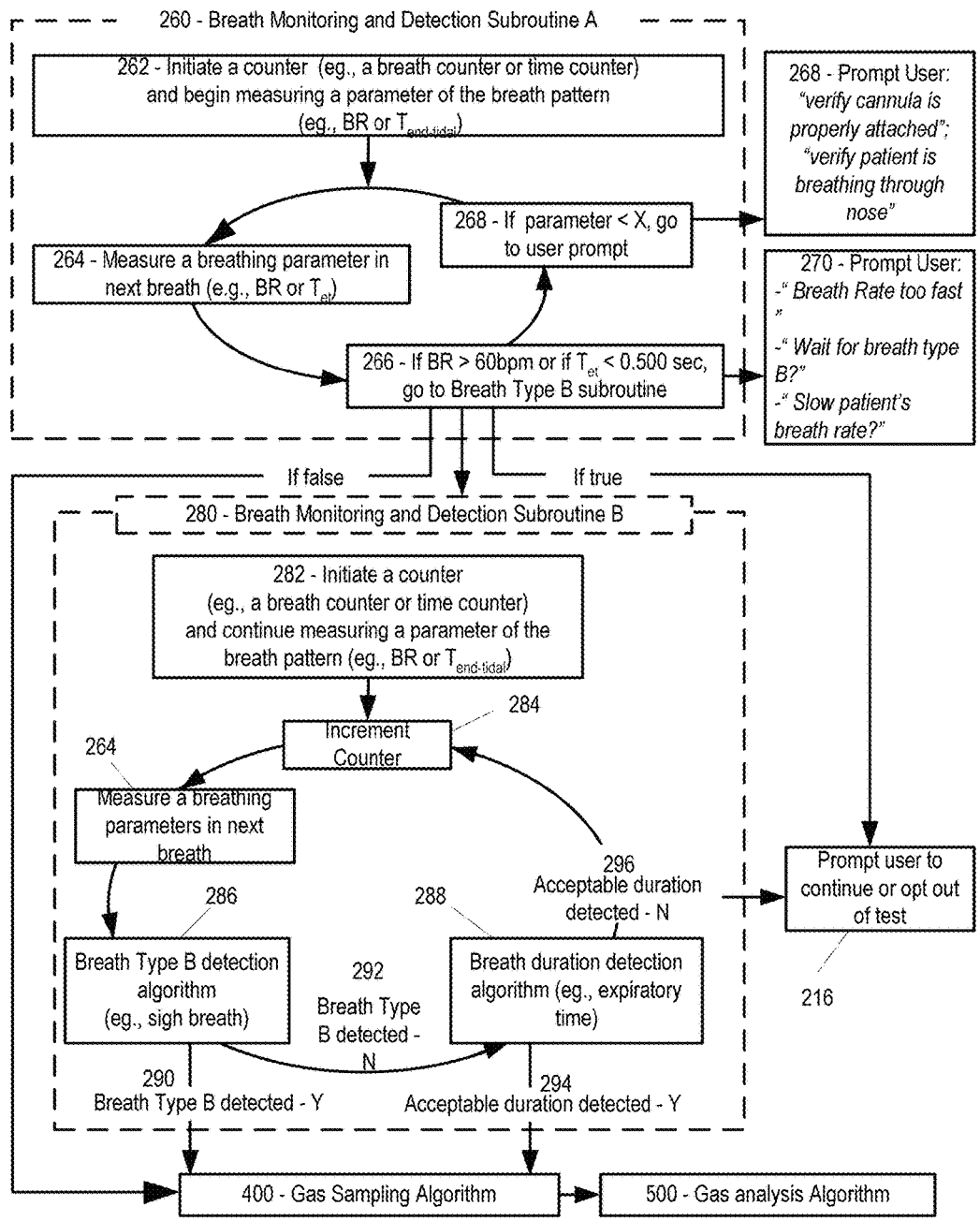
FIG. 16 describes an exemplary flow chart of a variation in which a second subroutine is invoked if the breath rate is too fast, in accordance with one variation.

FIG. 16 describes a flow diagram of one variation of a primary and secondary breath monitoring and detection subroutine 260 and 280 respectively, in accordance with one variation. In Subroutine A 260, a counter is initiated in Step 262, for example a breath counter or time counter, and a breathing pattern signal begins to be measured, for example breath rate or end-tidal time. In step 264, the breathing signal of the next breath is measured. In Step 266, the breathing signal measurement is compared to threshold values or criteria and a determination is made whether to transition to the capturing algorithm 400, or to prompt the user or to transition to the other Subroutine 280. In Subroutine A 260, if the breath criteria are not met, the user may be prompted to verify that the system is set up correctly, and the user may also be prompted to wait, or make adjustments with the patient, for example body position, or wait until the patient is not agitated. If the breath criteria are still not met, the system may enter a second subroutine, Subroutine B, in which an alternate type of breath is searched for, for example a sigh breath. Once found, the end-tidal section of the breath may be captured and analyzed, and correction factors are applied to the result if needed. For example, if it is determined that the criteria are not met in Step 266, in Step 268 the system commands the user interface 30 to prompt the user of the breath detection status. For example, in Step 266, the criteria may be breath rate less than 60 bpm and end-tidal time greater than 0.5 seconds. If not met, Subroutine B 280 may be eventually invoked. However, before Subroutine B is invoked, Step 266 may command the user interface to display messages in Step 270 such as "breath rate too fast" or "slow patient's breath rate" or ask the user for example if they want to "wait for breath type A?" or "invoke algorithm B?". In Step 268, if various criteria are not met which indicate a weak or missing signal, the system may command the user interface to display messages in Step 268 such as "verify cannula is attached", or "verify patient is breathing through cannulated nostril."

In Subroutine B, 280, a counter is initiated in Step 282, for example a breath or time counter, and a first breath is measured. In Step 284 the counter is incremented. In Step 264 a next breath is measured. In Step 286 the measured breath is compared to Algorithm B's breath monitoring and detection criteria, and if satisfied in Step 290 the breath is sampled in Step 400. For example, in Step 286, the criteria may be looking for a sigh breath. If the criteria are not satisfied as shown in Step 292, another set of criteria are applied to the measured breath in Step 288, for example a certain expiratory time requirement. If met as shown in Step 294 the breath is sampled in Step 400, however if not met as shown in Step 296, the cycle continues on to measure the next breath, and or the system prompts the user with the option to opt out as shown in Step 216.

Figure 17:
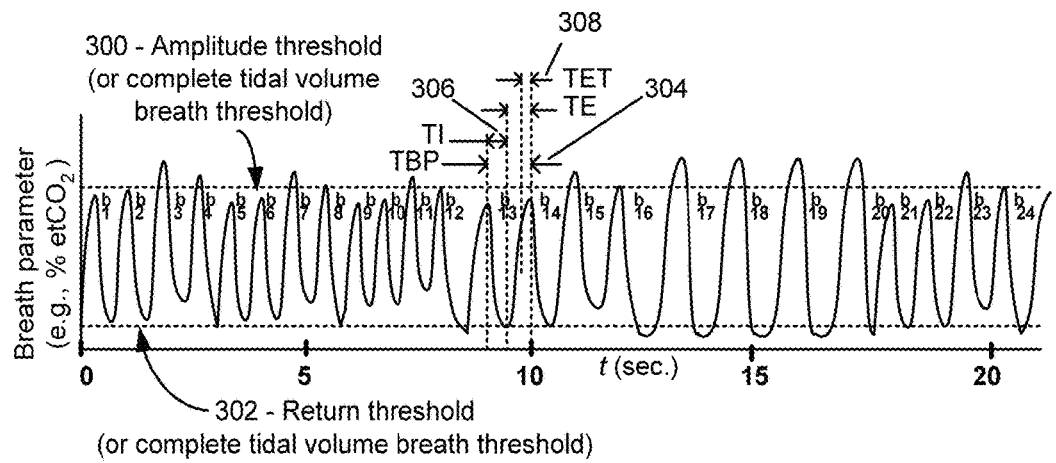
FIG. 17 describes a breathing signal from a series of breaths showing breaths that may be too fast for end-tidal capture and analysis, or that may not be complete tidal volume breaths, as well as breaths that may be desirable targets for end-tidal sample capture and analysis, in accordance with one variation.
Figure 18:
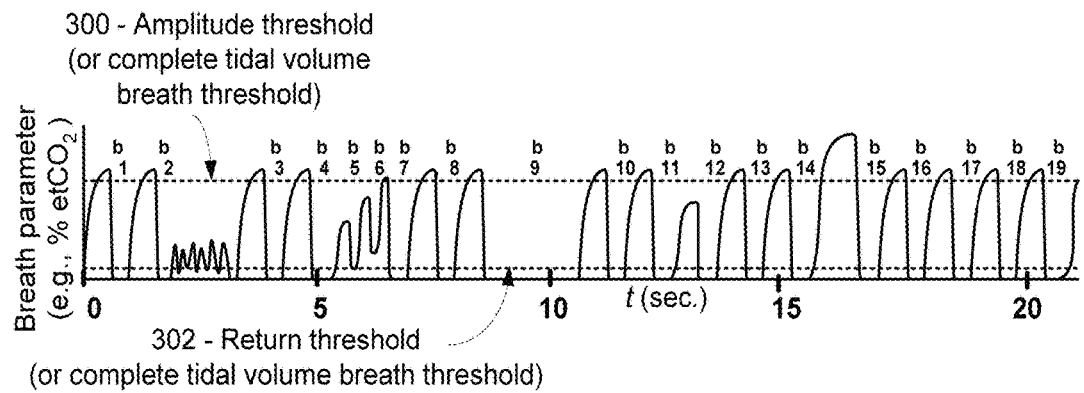
FIG. 18 describes a breathing signal from a series of breaths showing breaths that may be too erratic or physiologically non-representative for analysis, as well as breaths that may be desirable targets for end-tidal sample capture and analysis, in accordance with one variation.

FIGS. 17 and 18 describe examples of valid and invalid breaths with respect to whether or not the end-tidal portion of the breath is representative of the alveolar gas concentrations. Various breath signal criteria, including amplitude and frequency criteria, are included in the breath detection and targeting algorithms, are included in order to disqualify "invalid" breaths and qualify "valid" breaths. The criteria may include trending of breaths and comparison of a current breath to the recent trend, and comparison against default threshold values and alternatively against customized threshold values based on the test's prevailing circumstances. It may be beneficial to target a breath that meets a complete normal tidal volume breath and also may be beneficial to target a breath in the midst of steady state breathing after a number of complete normal tidal volume breaths, to assure steady state conditions of the gas composition in the breath has been reached or re-established.

FIG. 17 is a timing diagram describing an erratic breathing pattern, for example from a neonatal patient, in accordance with one variation. The breathing parameter signal measurement is shown on the vertical axis and may be for example a $CO_2$ signal. The breath monitoring and detection algorithms may set threshold criteria for the $CO_2$ signal to classify breaths as valid or invalid for sampling purposes. The threshold criteria may be a signal's peak amplitude 300 or amplitudes, a signal baseline level 302 or levels, and various frequency or time related parameters such as thresholds for the inspiratory time TI, the breath period time TBP, the expiratory time TE and or the end-tidal time TET, 306, 304, 308 and 310 respectively. As shown in the graph, breaths b1-b11 may be too short in duration for the system to realistically capture an accurate end-tidal sample from these breaths. The average breath rate of this series of breaths is 96 bpm, which would make the exhalation portion of the waveform for these breaths approximately 0.313 seconds in duration. Given that the end-tidal section of exhalation is the latter half of exhalation, only a fraction of the 0.313 second would be the appropriate section to target an end-tidal sample, which may yield an unreliable sample. Breaths this fast even for neonates may not be complete tidal volume breaths; rather they may be partial breaths, or hyperventilation breaths, or mostly deadspace breaths, in which case the end-tidal gas, even if it could be accurately collected, will not be representative of alveolar gas and will instead have more deadspace gas. Therefore, it may be inaccurate and undesirable to perform an end-tidal measurement on any of the breaths b1-b11. In order to screen out such rapid and incomplete breaths, breath signal amplitude thresholds can be set to define a complete tidal volume breath, for example, reaching a certain peak during the expiratory phase, and reaching a certain valley during inspiratory phase, as well as staying above and below those thresholds respectively for an appropriate period of time. Now turning to breaths b12-b16, while breath b16 appears to meet both proposed thresholds, it is preceded by erratic and inconsistent breathing, and while it may be a complete tidal volume breath, the end-tidal gas in that breath may not have reached steady-state gas composition levels. Now turning to breaths b17-b19, three consecutive breaths meet the tidal volume threshold requirements, and in this example it is proposed that breath b19 has reached steady-state end-tidal gas composition levels, and is a clinically representative breath to target, acquire and measure.

FIG. 18 shows an additional example of a series of breaths b1-b19, including physiologically representative breaths and non-representative breaths, in accordance with one variation. An example of breath signal noise is described between breaths b2 and b3. This noise may for example be sensor noise, sensor noise accompanied by an apneic period, patient movement, cannula movement, noise from coughing or other high frequency breath related noise, or cardiogenic noise. These waveforms may be disqualified for sampling as they may not produce a valid alveolar gas sample. Breath b3 meets the threshold criteria described previously in FIG. 17, however, the gas composition of breath b3 may be out of balance because it followed the noise, so breath b3 may be disqualified by the breath targeting algorithms. Breaths b4-b6 describe breath stacking where the next breath begins prior to completion of the prior breath. The end-tidal gas in breaths during breath stacking may not be representative of alveolar gas and may be dismissed. Breath b7 and b8 following the breath stacking may still be out of balance and may be dismissed as well. Breath b9 is characteristic of an inspiratory breath hold, or an inspiratory sigh, a post expiratory period, or an apneic period. The exhaled gas from breath b9 may need to be disqualified, depending on the diagnostic test being conducted, as the end-tidal gas may contain a higher than normal alveolar gas concentration since gas in the blood has had a longer time to diffuse into the alveoli. Breath b10 may be dismissed by the targeting algorithm as well because of the risk their gas compositions have not yet returned to normal. Breath b11 is a partial incomplete breath, smaller than the average normal breath, and is also dismissed by the targeting algorithms, and breaths b12 and b13 may be dismissed because of the risk they have not returned to their normal gas compositions. Breath b14 is a larger than normal breath and may be dismissed by the algorithms. Finally, there is a series of 3 or more consecutive normal breaths that meet the threshold criteria, and breath b18 can be targeted for sampling. Other permutations of the above targeting and breath qualification algorithms may be used as well. For example, the number of breaths before a sample is taken may be varied.

Figure 19:
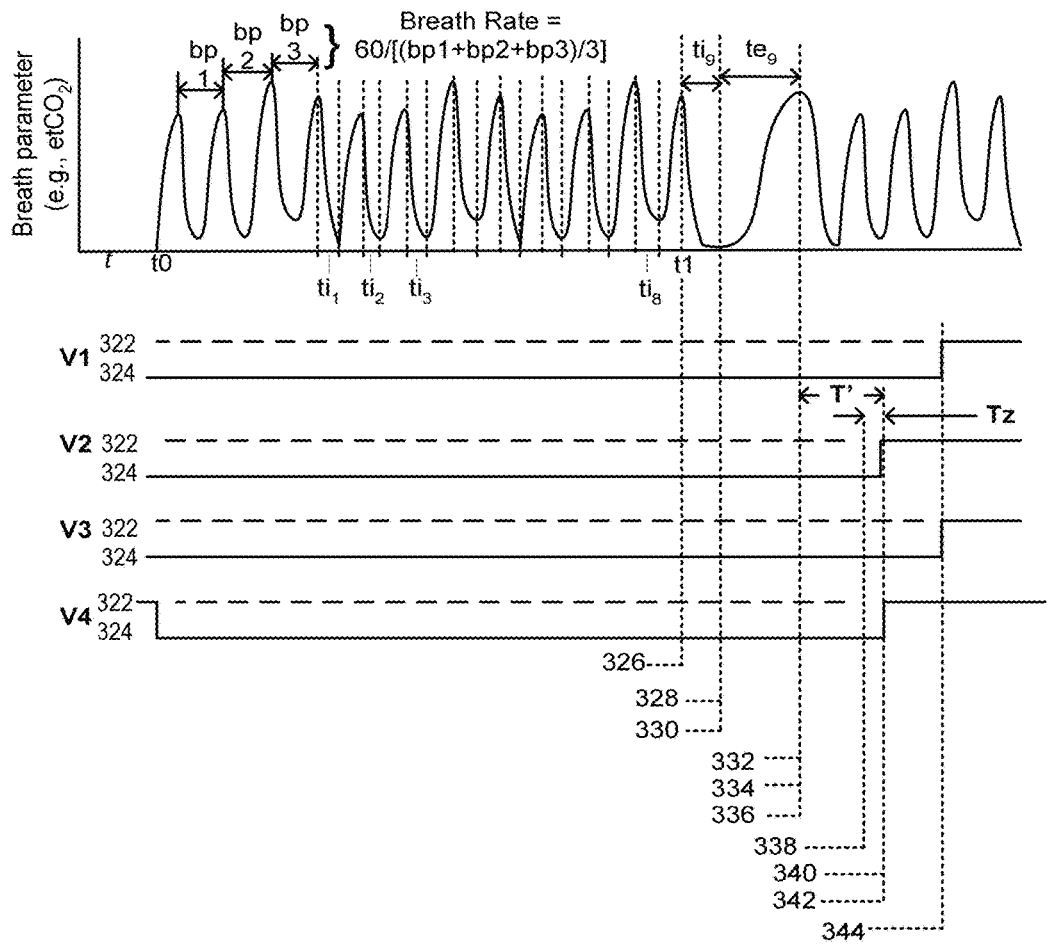
FIG. 19 describes a timing diagram of an example of a monitoring and capture system that searches for and captures the end-tidal gas following a sigh breath, in accordance with one variation.

In the foregoing descriptions, a sigh breath may be disqualified because its end-tidal gas may not be representative of the steady-state alveolar gas concentrations. However, in some physiological states and clinical conditions it may actually be beneficial to target a sigh breath. In these situations, the breath may be a more accurate representation of alveolar gas, or in other situations, the sigh breath may be the only type of breath that can be realistically captured for analysis, and a correction factor may be applied to convert the measured result to the true physiological value. FIG. 19 describes a variation in which a system acquires an end-tidal gas sample from an exhaled breath following a sigh inspiration. As shown in the top tracing, the breathing pattern is relatively erratic and the breath rate relatively fast between t0 and t1, as determined by measuring the breath rate, for example a three breath running average as shown for the first three breath periods bp1, bp2 and bp3. As a result, the end-tidal portion of the breathing pattern is not pronounced or defined enough to reliably capture a sample from the end-tidal period, and or to capture an end-tidal sample volume that is sufficient enough in volume for accurate analysis by the sensor. In the example shown in FIG. 19, because the breath pattern is too erratic and or too rapid, a criterion may be established to monitor for the occurrence of a sigh breath. For example, the inspiratory times of the breaths are measured and compared against a threshold time and if the threshold is met or exceeded, the breath may be classified as a sigh breath. The threshold time may be for example 250% of the average historical inspiratory time. The threshold criteria used to determine if a breath is a sigh breath may be, for example, an inspiratory time value that is established based on historical inspiratory times, for example 150% of the average inspiratory time of the last 3 breaths. Alternatively it can be an inspiratory time value that is predefined based on normal values. For example the average inspiratory time of three sequential breaths, shown as ti1, ti2 and ti3 may be used to establish an average to which a potential sigh breath is compared. In the example shown the inspiratory time ti9 displays a considerable increase over the average of the three previously mentioned, and thus the exhalation following ti9, should be considered a potential sigh breath exhalation. Measuring its expiratory time, te9 will help in the assessment of whether or not it is a sigh breath. Expiratory time te9 can be compared to previous expiratory times. Or alternatively a sigh can be determined by the amplitude of the inspiratory signal, for example if an airway pressure signal is a larger negative value than normal. Once the sigh breath occurs, the following exhalation may be targeted for acquisition of a gas sample from the end-tidal section.

The valves V1-V4 shown in the lower tracings in FIG. 19 control the various sequences of operation including monitoring of the breathing pattern, acquiring the end-tidal sample into the sample tube, and pushing the sample to the gas analyzer. As will be readily understood by one of skill in the art, valves V1-V4 are used for explanatory purposes and systems with more or less valves could be used and the timing adjusted accordingly. The valves may be 3 position valves as shown in FIGS. 1 and 7, with a common port c always open, and with either port a or b open at any given time. At time 326 an inspiratory time counter is initiated. At time 328 the inspiratory time counter is ended. At time 330 an expiratory time counter is initiated. At time 332 the end of the expiratory gas is detected exiting the breathing sensor, such as a Capnometer. At time 334, the expiratory time counter is terminated. At time 336 a sample travel time counter is initiated, tracking the time of travel of the gas sample from the breathing sensor to the sample tube. At time 338, Tz seconds before time 340, a command is sent to the appropriate valves to isolate the desired gas sample from other gases in the system. At time 340, T' seconds after time 332, the end of the end-tidal gas sample has reached the entrance to the sample tube, or valve V2. At time 342 a command is sent to switch the valve ports such that gas does not flow through the sample tube 18, and gas comes in from the ambient inlet (see FIGS. 1 and 7). At time 344 all valves are switched to port b being open so that the sample is pushed by ambient air to the sensor for compositional analysis. The exhaled gas after a sigh inspiration may beneficially provide a good source of gas for an ETCO measurement for a number of reasons. First, the exhalation time and end-tidal time is likely to be extended, making targeting the end-tidal portion relatively easy and therefore potentially more accurate for certain diagnostic tests. Second, the depth of inspiration during the sigh fills the alveoli more than normal, thus providing more end-tidal volume in the subsequent exhalation than an average end-tidal volume, thus potentially providing a richer end-tidal sample for analysis. Third, there is typically longer residence time of the gas in the alveoli during a sigh inspiration, compared to a normal breath, and this longer residence time allows for more gas exchange from the blood stream into the alveoli, and therefore the ETCO measured in the end-tidal gas may provide a more accurate representation of blood CO then the ETCO measured in the end-tidal portion of a normal breath. Fourth, sigh breaths have a tendency to recruit areas of the lung that are atellectactic or not fully inflated. Therefore, the end-tidal gas in exhalation after a sigh breath may be more representative of the entire lung in certain clinical situations, and therefore possibly more representative of the CO in the blood stream.

Figure 20:
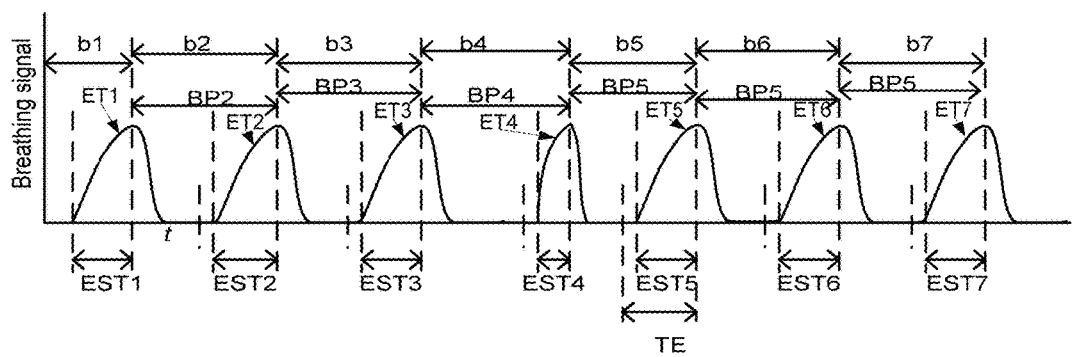
FIG. 20 is a breathing signal graph versus time which shows the use of an expiratory signal parameter to determine if the breath is representative or not, in accordance with one variation.

FIG. 20 describes a graph of a breathing parameter signal amplitude over a sequence of seven breaths b1 through b7, in accordance with one variation. In FIG. 20, an end-tidal section of gas is depicted as ET1 through ET7, an expiratory signal time parameter is depicted as EST1 through EST7, and expiratory time is depicted as TE. As can be seen in the graph, the breath period, BP4, of the fourth breath, b4, appears to be equal to the breath period of the three preceding breaths, and therefore breath four may be deemed to be a representative breath from which a valid end-tidal gas measurement can be taken. However, upon closer inspection, breath four is actually non-representative of the historical typical breaths, as indicated by an expiratory signal parameter EST4. The shorter EST4 of breath b4, which corresponds to a longer than average inspiratory time, for example an inspiratory hold or pause, may result in an end-tidal concentration that is not representative of the alveolar gas. Breath b7 which is preceded by two apparently representative breaths likely consists of end-tidal gas that has reached steady-state and is representative of alveolar gas. In order to prevent inadvertent capturing of non-representative breaths, and assure capturing of representative breaths due to the above paradigm, some variations utilize an expiratory time signal rather than or in addition to the breath period in order to determine if the breath is a representative target or not. The expiratory time signal may be the expiratory duration, the duration of the rise of the signal, or other frequency related parameters associated with the expiratory phase of the breathing signal.

Figure 21:
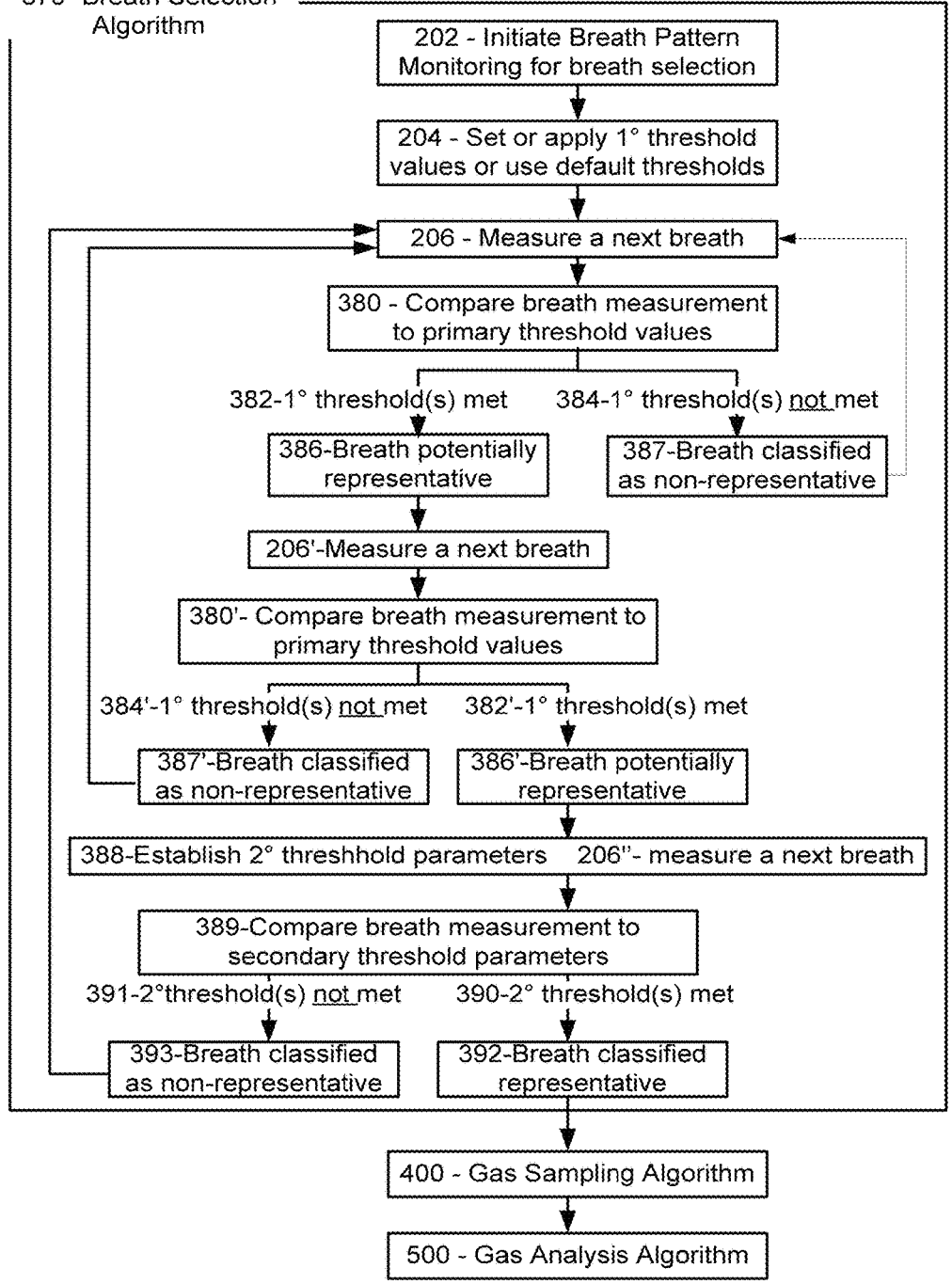
FIG. 21 is a flow diagram describing a multi-part algorithm for selecting a breath, the algorithm including a first step to classify a potentially physiologically representative breath, a second step of classifying a subsequent breath as potentially physiologically representative, and a third step of classifying the subsequent breath as physiologically representative, in accordance with one variation.

FIG. 21 describes breath selection algorithm 379, in accordance with one variation. Algorithm 379 comprises at least two stages. In the preliminary initialization steps, in Step 202 the breath pattern monitoring is initiated, in Step 204 a set of primary threshold values are applied or default values are used, and in Step 206 a next breath is measured accordingly. The primary threshold values may be amplitude and timing values, for example. Steps 380 to 387 describe the first main stage of the algorithm 379. After initialization and during and after the measurement of a first breath, in Step 380 the breath is compared to the set of primary threshold values. In Steps 382 and 384 the determination is made if the measured breath meets the threshold criteria or not, respectively, and in steps 386 and 387 the measured breath is classified as representative or non-representative respectively. If non-representative, the algorithm returns to Step 206. If representative, the algorithm moves on to the second Stage beginning with Step 206' measuring a next breath. In Step 380', the measured breath is compared to the primary threshold parameters. The primary threshold parameters may be the same parameters as in Step 380, or might be revised or updated between measurements. In Steps 382' and 384' a determination is made whether the primary threshold parameters are met or not respectively. In Steps 386' and 387', the breath is classified as potentially representative or non-representative, respectively. Should the breath be classified as non-representative, the algorithm returns to step 206, otherwise the breath may move on to a third Stage of the algorithm. In the third Stage, a set of secondary breathing signal threshold parameters are established in Step 388 and in Step 206" a next breath is measured. The secondary threshold parameters may be for example breath signal amplitude and or timing values that are established based on the potentially representative breath classified in Step 386. In Step 388 a comparison is then made between the potentially representative breath which was classified in Step 386' to the previous potentially representative breath classified in Step 386. In Steps 390 and 391 a determination is made if the breath measured in Step 206" meets the secondary threshold parameters, and if so, the breath is classified as representative and is sent on for sampling and measurement, otherwise, the algorithm returns to Step 206.

In the multi-stage algorithm 379 described in FIG. 21, for example, the primary threshold values may be breath signal amplitude and durations of portions of the breath signal, in order to verify that a breath waveform is not an artifact and not an abnormal breath such as a sigh breath, a partial breath, or a breath hold breath. If a breath meets the threshold values, then the next breath is likewise evaluated. If the next breath also meets the threshold values, it can then be compared against the first breath to verify that the breathing pattern is stable. Therefore, the secondary threshold parameters may be that of a comparison against the previous breath, assuming the previous breath met the primary threshold values. The comparison can be for example in signal amplitude indicative of breath depth, and or signal duration indicative of breath period or breath rate. This may reduce the risk of sampling a breath that is not a regular tidal volume breath, or not of the breath type desired. Moreover, the routine may help make sure that the breath ultimately sampled was taken from a breath after another normal breath, thus potentially avoiding the effect that an abnormal breath would have on the composition of a subsequent normal breath. The comparison to previous breaths in the example shown is a comparison to one previous potentially representative breaths, but the comparison can also be to more than on previous potentially representative breaths, not necessarily in sequence. For example, a $10^{th}$ breath may be compared to a $3^{rd}$, $5^{th}$ and $7^{th}$ breath which were each classified as potentially representative, and in which case the other intervening breaths were deemed non-representative based on the primary threshold parameters.

In addition, in situations in which the sample collected in the sample tube is not a pure end-tidal sample and is diluted with pre-end-tidal exhaled gas, the dilution can be corrected for using an expiratory signal parameter such as EST4 shown in FIG. 20, rather than using the breath rate based on the breath period BP4. This dilution correction technique may beneficially increase the accuracy of the correction since the sample tube dilution may be more dependent on the expiratory duration than the breath period duration.

As used herein, the term end-tidal can be understood to refer to a section of an exhaled breath that is at or near the end of the expiratory period, and may be after the deadspace has been exhaled from the person. SuFurther, in addition to measuring gases such as CO in the end-tidal gas exemplified throughout the specification, it is also contemplated that non-gases such as particulates and other chemicals may be measured in the same or similar manner.

Figure 22:
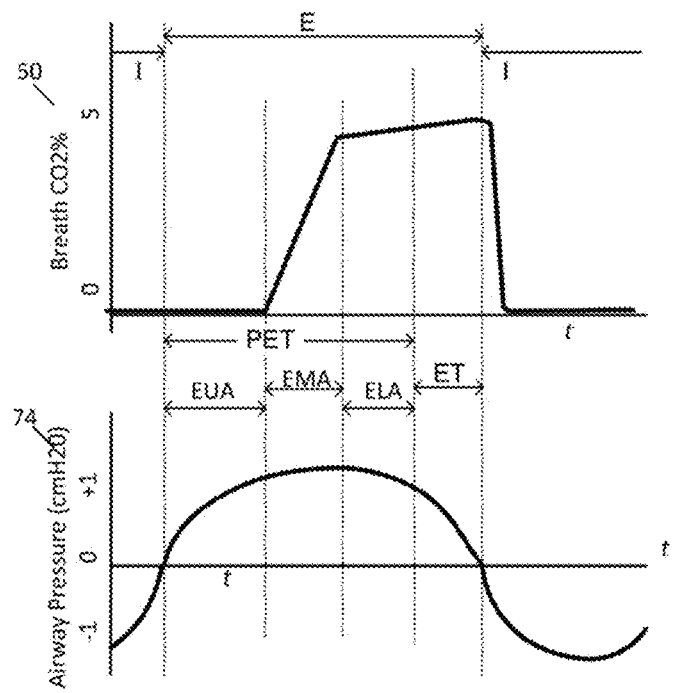
FIG. 22 graphically describes breathing pressure signals used to identify different sections of exhalation corresponding to gas from different sections of the lung being exhaled, in accordance with one variation.

FIG. 22 graphically describes breathing pressure signals used to identify different sections of exhalation corresponding to gas from different sections of the lung being exhaled, in accordance with one variation. In some cases in may be desired to measure gas or other analytes stemming from different sections of the lung besides the end-tidal section. For example, analytes from the upper airway may be indicative of upper airway respiratory problems like asthma or airway disorders and diseases. Analytes from the middle airways between the upper airways and the lower bronchioles may be indicative of for example forms of lung cancer or analytes stemming from the stomach getting into the airways from the esophagus, and analytes from lower airways may be indicative of yet other syndromes like lung infections or potentially systemic problems. Further, comparison of one compartment to another may be useful in understanding an underlying disease or condition. In the example shown the top tracing is a capnometry signal and the lower tracing is an airway pressure signal, although the measurement can be other types of signals such as oxygen, temperature, or acoustic. Using one of, or a combination of the signals, the expiratory phase E can be separated into various portions of exhalation, for example exhalation of upper airway gases, middle airway gases, lower airway gases and end-tidal gases, labeled EUA, EMA, ELA, and ET respectively. For example the start of the exhalation of upper airway gas can be discerned by a positive increase in airway pressure, and the end of the upper airway gas exhalation can be discerned by an increase in the exhaled CO2 level. The start of exhalation of the middle airway gas EMA may be discerned by an increase in the CO2 level and the end of exhalation of the middle airway gas may be discerned by reaching a plateau in the airway pressure signal. The start of exhalation of the lower airway gas may be discerned by a decrease in the airway pressure signal and the end of exhalation of the lower airway gas may be discerned by a change in slope of the airway pressure signal or a certain rise in the CO2 signal.

Figure 23:
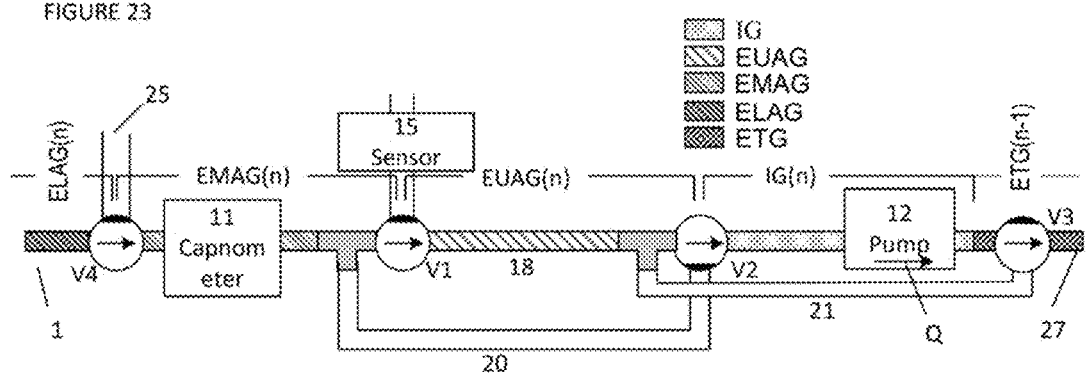
FIG. 23 shows a pneumatic schematic of the system shown in FIG. 1 and in which the system is used to target, isolate and measure an analyte from any portion of the breathing curve, as described in FIG. 22.

FIG. 23 shows a pneumatic schematic of the system shown in FIG. 1 and in which the system is used to target, isolate and measure an analyte from any portion of the breathing curve, as described in FIG. 22. In the example shown, breath n is targeted by the procedures and techniques explained in the forgoing descriptions. In this case the desired diagnostic test is examining the upper airway for an analyte indicative of an inflammatory disease such as asthma. Expiratory gas from the upper airway from breath n, EUAG(n) is isolated in the sample tube 18, and later shuttled to the sensor 15 for compositional analysis. In this case the analysis may be of NO gas, or other analytes related to inflammatory response. In the schematic example shown, the inspiratory gas IG(n) and other sections of the expiratory gas EMAG(n), ELAG(n) from breath n, and end-tidal gas from the previous breath ETG(n−1) are elsewhere in the system and isolated from the gas sample in sample tube, so as to not disturb the homogeneity of the targeted sample. While some diseases, conditions, gases or analytes have been mentioned in conjunction with FIGS. 22 and 23 as well as the preceding Figures, these have been mentioned as examples only and the system, apparatus, algorithms and methods described can be used to sample and measure any analyte of interest for any disease or condition of interest.

As will be readily understood by those of ordinary skill in the art, the devices described herein are offered by way of example only and other devices could be used to implement the methods and systems described herein. Moreover, although the device described may be used to illustrate certain features of the disclosure, it should be understood that the methods and systems disclosed here are not limited to a specific device.

Although some variations are discussed by reference to algorithms, it should be understood that the descriptions cover corresponding methods and apparatuses that embody the variations.

Further, although variations above may be discussed with reference to identifying a portion of gas and then analyzing the gas, it should be understood that some variations may not include an analysis portion. In some variations, the gas is stored without analysis, for example, the gas may be transported to a remote location for analysis. A stored gas should be understood broadly and includes at least storing prior to analysis and storing for transport.

In the foregoing descriptions of variations of the invention, it should be noted that it is also conceived that the sequences of operation described in the Figures can be combined in all possible permutations. In addition, while the examples describe ETCO measurement they may apply to other gases, for example hydrogen. Additionally, while some variations may apply to $CO_2$ measurements, it should be understood that the apparatuses and methods described herein could be applied to a direct CO sensor. The examples provided throughout are illustrative of the principles of the invention, and that various modifications, alterations, and combinations can be made by those skilled in the art without departing from the scope and spirit of the invention. Any of the variations of the various breath measurement and sampling devices disclosed herein can include features described by any other breath measurement and sampling devices or combination of breath measurement and sampling devices herein. Accordingly, it is not intended that the invention be limited, except as by the appended claims. For all of the variations described above, the steps of the methods need not be performed sequentially.

The invention claimed is:

1. An apparatus for analyzing an exhaled breath, comprising:
    a sensor;
    a breath sampling system;
    a gas analyzer; and
    a control system comprising a processor that operates the sensor, the breath sampling system, and the gas analyzer using a plurality of algorithms,
    wherein the sensor measures a first parameter of a first exhaled breath to determine a threshold criteria according to a first algorithm run by the processor, the sensor also measuring a second parameter of a next exhaled breath,
    wherein the breath sampling system captures the next exhaled breath according to a second algorithm run by the processor when the second parameter meets the threshold criteria, or initiates capture of an alternative breath according to a third algorithm when the threshold criteria are not met, and
    wherein the gas analyzer
    applies a gas sampling and analysis algorithm to the captured next exhaled breath, and applies a correction factor to the gas sampling and analysis algorithm for the captured alternative breath.

2. The apparatus of claim 1, further comprising a physiologic sensor that monitors a physiological parameter of a patient, wherein the breath sampling system captures the next exhaled breath when a fourth algorithm determines the physiological parameter meets a predetermined physiological criteria.

3. The apparatus of claim 2, wherein the physiologic parameter comprises at least one selected from the group consisting of a blood pressure, a heart rate, chest impedance, a weight, a height, an age, a race, a sex, a diagnosis, a respiratory rate, a tidal volume, a minute volume, an inspiratory:expiratory ratio, a blood gas, a cardiac output, an end tidal $CO_2$ concentration, a pulmonary perfusion, a base excess, an $O_2$ saturation, and a ventilation:perfusion ratio.

4. The apparatus of claim 1, wherein the predetermined criteria comprises a minimum duration.

5. The apparatus of claim 1, wherein the predetermined criteria comprises at least one selected from the group consisting of: a peak amplitude value, a baseline value, a time duration above the peak amplitude value, a time duration below the baseline value, and a percent comparison of a current breath to a trending algorithm.

6. The apparatus of claim 1, wherein the predetermined criteria comprises an amplitude value and a baseline value representing a complete tidal volume breath.

7. The apparatus of claim 1, wherein the predetermined criteria comprises a breath rate of less than or equal to 60 breaths per minute.

8. The apparatus of claim 1, wherein the threshold criteria are based on at least one selected from the group consisting of an expiratory time, a portion of an expiratory time, an airway pressure, a $CO_2$ value over time, an $O_2$ value over time, an airway temperature, a breath flow rate, a breath rate, a depth of breath, a duration of breath, an inspiratory time, a pre-end-tidal time, an end-tidal time, a post-expiratory time, an inspiratory pause, a peak inspiratory pressure, a peak expiratory pressure, a characteristic waveform for sneeze, cough, stacked breath or non-full breath, an inspiratory amplitude, an expiratory amplitude, and a historical breath criteria.

9. The apparatus of claim 1, wherein the predetermined criteria is based upon at least one selected from the group consisting of a breath hold, a deep breath, a forced exhaled breath, an inspiratory pause, an expiratory pause, a resting respiration, and a breath pattern repetition.

10. The apparatus of claim 1, wherein the predetermined criteria is based upon a predetermined number of repetitive breaths.

11. The apparatus of claim 10, wherein the number of repetitive breaths is between 1 and 5 breaths.

12. The apparatus of claim 10, wherein the number of repetitive breaths is between 2 and 4 breaths.

* * * * *